United States Patent
Hwang et al.

(10) Patent No.: US 12,203,830 B2
(45) Date of Patent: Jan. 21, 2025

(54) SENSORS WITH DEHUMIDIFIERS

(71) Applicant: University of Pittsburgh-Of the Commonwealth System of Higher Education, Pittsburgh, PA (US)

(72) Inventors: Sean Ihn Young Hwang, Cambridge, MA (US); Alexander Star, Pittsburgh, PA (US); Sung Kwon Cho, Pittsburgh, PA (US); Hou-Yu Chen, Victoria, TX (US)

(73) Assignee: University of Pittsburgh Of the Commonwealth System of Higher Education, Pittsburgh, PA (US)

( * ) Notice: Subject to any disclaimer, the term of this patent is extended or adjusted under 35 U.S.C. 154(b) by 261 days.

(21) Appl. No.: 17/775,391

(22) PCT Filed: Nov. 8, 2020

(86) PCT No.: PCT/US2020/059591
§ 371 (c)(1),
(2) Date: May 9, 2022

(87) PCT Pub. No.: WO2021/092528
PCT Pub. Date: May 14, 2021

(65) Prior Publication Data
US 2022/0397493 A1    Dec. 15, 2022

Related U.S. Application Data

(60) Provisional application No. 62/932,997, filed on Nov. 8, 2019.

(51) Int. Cl.
*G01N 1/22* (2006.01)
*A61B 5/08* (2006.01)
*G01N 35/00* (2006.01)

(52) U.S. Cl.
CPC ........... *G01N 1/2202* (2013.01); *A61B 5/082* (2013.01); *G01N 1/2214* (2013.01);
(Continued)

(58) Field of Classification Search
CPC ....... G01N 2035/00455; G01N 1/2022; G01N 1/2214; G01N 1/2244; G01N 1/2282; G01N 1/2202; A61B 5/082
See application file for complete search history.

(56) References Cited

U.S. PATENT DOCUMENTS

| 3,596,888 A | 8/1971 | Heller |
| 4,586,342 A * | 5/1986 | Morishita ............... F25B 21/02 62/3.4 |

(Continued)

FOREIGN PATENT DOCUMENTS

| CN | 201569203 | 9/2010 |
| WO | WO-2017189546 A1 * | 11/2017 |
| WO | WO2021092528 | 5/2021 |

OTHER PUBLICATIONS

Zhu, Rong et al., Wireless Oxygen Sensors Enabled by Fe(II)-Polymer Wrapped Carbon Nanotubes, ACS Sens. 2017, 2, 1044-1050.

(Continued)

*Primary Examiner* — Justin N Olamit
(74) *Attorney, Agent, or Firm* — BARTONY & ASSOCIATES, LLC

(57) ABSTRACT

A sensor system for detecting at least one analyte in an environment includes a dehumidifier system including at least one of a condenser unit and a desiccant unit and a sensor responsive to the analyte in fluid connection with the dehumidifier system.

21 Claims, 14 Drawing Sheets

(52) U.S. Cl.
CPC ............ *G01N 2001/2244* (2013.01); *G01N 2001/2282* (2013.01); *G01N 2035/00455* (2013.01)

(56) References Cited

U.S. PATENT DOCUMENTS

| | | | |
|---|---|---|---|
| 5,375,421 | A | 12/1994 | Hsieh |
| 5,501,212 | A | 3/1996 | Psaros |
| 6,378,311 | B1 | 4/2002 | McCordic |
| 8,211,035 | B2 | 7/2012 | Melker |
| 8,739,558 | B2 * | 6/2014 | Enayati ............... F24F 11/67 62/3.4 |
| 10,244,964 | B2 | 4/2019 | Star |
| 11,264,224 | B2 * | 3/2022 | Chhabra ............... G01N 27/64 |
| 2011/0127446 | A1 | 6/2011 | Star |
| 2012/0065535 | A1 * | 3/2012 | Abraham-Fuchs ........................ G01N 33/497 600/532 |
| 2012/0122668 | A1 | 5/2012 | Celiker |
| 2012/0277612 | A1 * | 11/2012 | Li ............... A61B 5/4845 604/66 |
| 2015/0073290 | A1 * | 3/2015 | Star ............... A61B 5/7278 250/216 |
| 2016/0345910 | A1 | 12/2016 | Ahmad |
| 2018/0056302 | A1 | 3/2018 | Ahmad |
| 2020/0009342 | A1 | 1/2020 | Drew |

OTHER PUBLICATIONS

Peng, Gang et al., Detecting Simulated Patterns of Lung Cancer Biomarkers by Random Network of Single-Walled Carbon Nanotubes Coated with Nonpolymeric Organic Materials, Nano Lett., vol. 8, No. 11, 2008, 3631-3635.

Mendes, Maria Anita et al., A Cryotrap Membrane Introduction Mass Spectrometry System for Analysis of Volatile Organic Compounds in Water at the Low Parts-per-Trillion Level, Anal. Chem. 1996, 68, 3502-3506.

Evans, Gwyn P et al., Controlling the Cross-Sensitivity of Carbon Nanotube-Based Gas Sensors to Water Using Zeolites, ACS Appl. Mater. Interfaces 2016, 8, 28096-28104.

Costello, B. D., et al., "A Review of the Volatiles from the Heathy Human Body," J. Breath Res., 8, (2014), 1-30.

Toyooka, T et al., A prototype portable breath acetone analyzer for monitoring fat loss ; J . Breath Res . 7 ( 2013 ) , 1-8.

Snow, Eric S. et al. ; Capacitance and Conductance of Single-Walled Carbon Nanotubes in the Presence of Chemical Vapors ; Nano Lett ., vol. 5 , No. 12 , 2005 , 2414-2417.

Righettoni, Marco et al., Toward Portable Breath Acetone Analysis for Diabetes Detection ; J Breath Res . Sep. 2011 ; 5 ( 3 ) , 1-16.

Guirado-Lopez, Ricardo A et al., Interaction of Acetone Molecules with Carbon-Nanotube-Supported $TiO_2$ Nanoparticles : Possible Applications as Room Temperature Molecular Sensitive Coatings ; J . Phys . Chem . C 2007, 111,57-65.

Wang, L. et al.; Nanosensor Device for Breath Acetone Detection, Sensor Lett. 2010 , vol. 8 , No. 5, 1-4.

Righettoni, Marco et al.; Si : $WO_3$ Sensors for Highly Selective Detection of Acetone for Easy Diagnosis of Diabetes by Breath Analysis , Anal . Chem . 2010, 82, 3581-3587.

Galessetti et al., Breath Ethanol and Acetone as Indicators of Serum Glucose Levels : An Initial Report , Diabetes Technology and Therapeutics , vol. 7 , No. 1, 2005 , pp . 115-123.

Musa-Veloso et al., Breath acetone is a reliable indicator of ketosis in adults consuming ketogenic meals , Am J Clin Nutr 2002 ; 76 : 65-70.

* cited by examiner

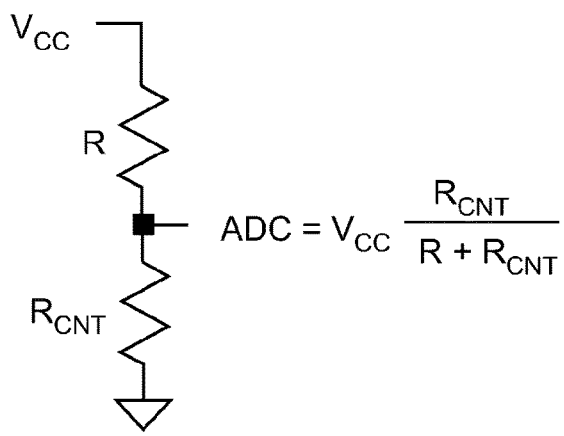
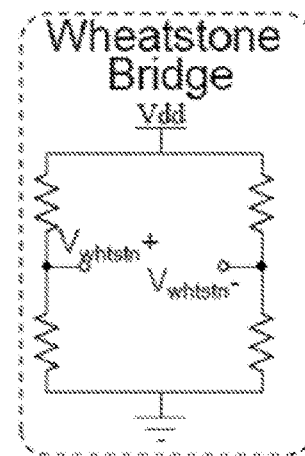
Fig. 8D
Fig. 8E
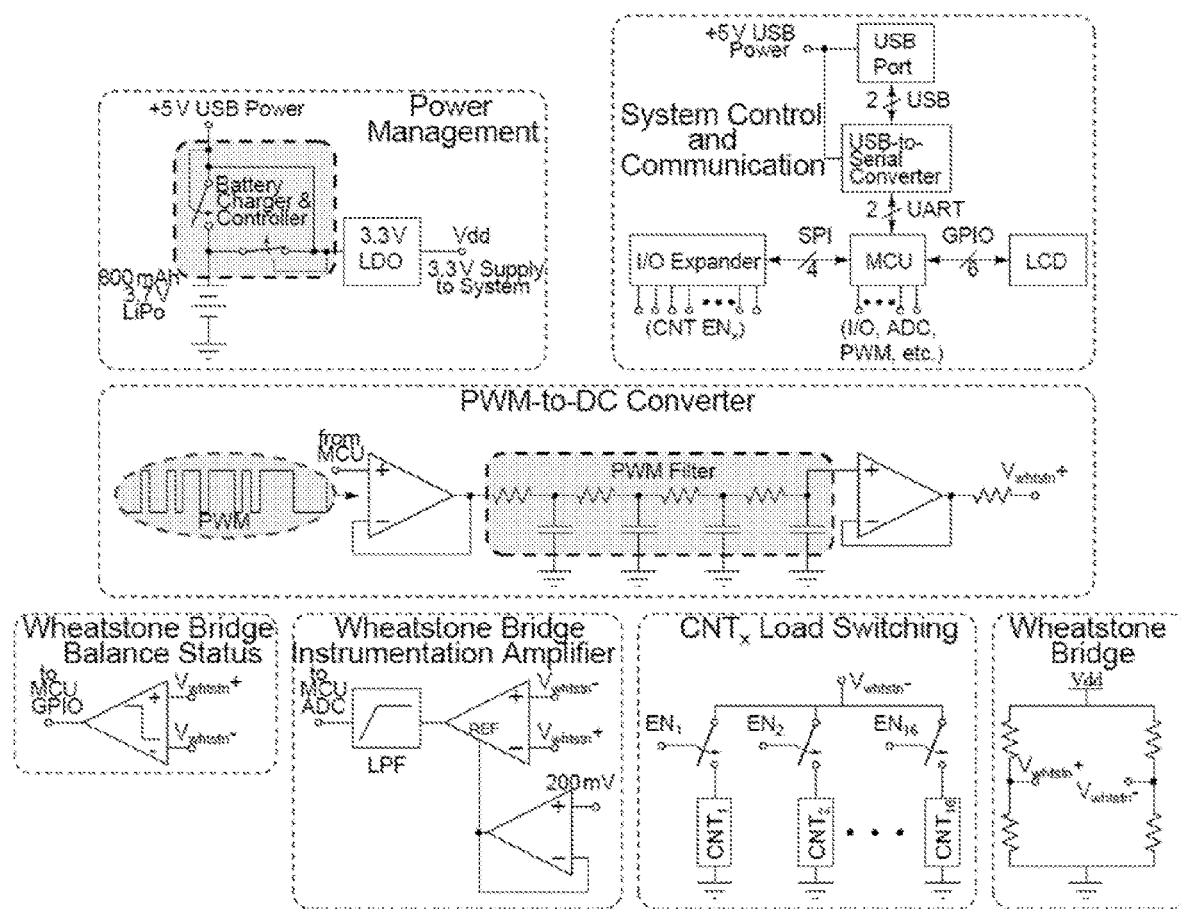
Fig. 8F

SENSORS WITH DEHUMIDIFIERS

CROSS-REFERENCE TO RELATED APPLICATIONS

This application is a national phase filing of PCT International Patent Application No. PCT/US2020/059591, filed Nov. 8, 2020, which claims benefit of U.S. Provisional Patent Application Ser. No. 62/932,997, filed Nov. 8, 2019, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Various sensors have been developed for use in a wide variety of environments. Recently a number of sensors in which a sensor medium of the sensor includes one or more nanostructures have been developed. Such sensors may, for example, exhibit relatively low lower limits of detections. Such sensors may, for example, be used in connection with human breath to detect various compositions in the breath which may be indicative of a patient's status.

Many sensors based upon nanostructures such as single walled nanotubes (SWNT; for example, single walled carbon nanotubes or SWCNT) are significantly cross-sensitive to water vapor/humidity changes. Moreover, sensors other than nanostructure-bases sensors may be quite cross-sensitive to changes in water vapor/humidity. Such cross-sensitivity can hinder or limit the application of such sensors in sensing an analyte or analytes of interest.

SUMMARY

In one aspect, a sensor system for detecting at least one analyte in an environment includes a dehumidifier system including at least one of a condenser unit and a desiccant unit and a sensor responsive to the analyte in fluid connection with the dehumidifier system. In a number of embodiments, the condenser unit includes a thermoelectric module having a cooling section positioned within a condensing chamber of the condenser unit, wherein the condensing chamber is in fluid connection with the environment and with the sensor. The desiccant unit may, for example, include a desiccant material positioned in fluid connection with a flow channel of the desiccant unit.

The dehumidifier system may, for example, include a plurality of condenser units, wherein each condenser unit includes a thermoelectric module. The plurality of condenser units may be arranged in series, in parallel or in a combination of series and parallel arrangements. In a number of embodiments, a condensing chamber of the condenser unit(s) further includes a desiccant material.

In a number of embodiments, the dehumidifier system includes a condenser unit including a thermoelectric module. The cooling section of each thermoelectric module includes a first heatsink in operative connection therewith and a heating section of the thermoelectric module includes a second heatsink in operative connection therewith. The heating section of each thermoelectric module may, for example, be positioned outside of the condensing.

The first heatsink may, for example, include an extending member which extends into the condensing chamber. The second heatsink may, for example, include a plurality of spaced plates or fins. The system may further include a fan in fluid connection with the second heatsink.

The first heatsink may, for example, include a plurality of spaced plates or fins. In a number of embodiments, the first heatsink includes a plurality of spaced plates or fins which define microchannels therebetween.

The dehumidifier system may, for example, include a desiccant unit including a desiccant material either with or without a condenser unit. In a number of embodiments, the desiccant material and a quantity of the desiccant material is selected to limit removal of the at least one analyte for a given range of flow rate so that a sample reaching the sensor includes a concentration of analyte at or above the detection limit of the sensor. In a number of embodiments, the desiccant material comprises calcium chloride.

In a number of embodiments, the desiccant system include a volume of the desiccant material positioned in a conduit so that a sample from the environment must pass through the desiccant material. The desiccant material may be chosen so that the analyte elutes through the desiccant material before significant water elutes therethrough over a range of time. Measurement of a response of the sensor may, for example, be timed to correspond with the range of time.

The sensor system may further include a drying system to remove at least a portion of at least one of condensate water or water adsorbed on the desiccant material.

In a number of embodiments, the at least one analyte is acetone. The environment may for example include a sample of breath or a body fluid and the analyte may, for example, be a volatile component thereof.

The sensor system may, for example, further include electronic circuitry to effect at least one of control of the sensor system and measurement of a response of the sensor.

In a number of embodiments, the sensor includes a substrate and a sensor medium on the substrate. The sensor medium includes at least one nanostructure. The substrate may, for example, include $SiO_2$ or a polymer. At least one property of the sensor medium is dependent upon the presence of the at least one analyte. The system may further include electronic circuitry including at least one measurement system in operative connection with the sensor to measure a variable providing a measure of change in at least one property of the sensor medium which is dependent upon the presence of the at least one analyte.

In a number of embodiments, the sensor medium includes a plurality of nanostructures in contact with titanium dioxide, and the sensor system further includes at least one energy source to apply electromagnetic radiation to the sensor medium for a period of time. The plurality of nanostructures may, for example, include carbon nanostructures. The titanium dioxide may, for example, be mixed with the nanostructures, immobilized upon the nanostructures, or covalently attached to the nanostructures. In a number of embodiments, the plurality of nanostructures comprises a network of oxidized single-walled carbon nanotubes. The measured variable may, for example, be an electrical property change.

In a number of embodiments, the electromagnetic radiation source is a source of UV light. A baseline for detection of the at least one analyte may, for example, be established after application of UV light for the period of time.

In a number of embodiment, titanium dioxide is deposited upon the nanostructures via sol-gel synthesis.

In another aspect, a method of detecting an analyte in an environment includes passing a sample from the environment through a dehumidifier system comprising at least one of a condenser unit and a desiccant unit and contacting the sample with a sensor in fluid connection with the dehumidifier after the sample exits the dehumidifier system.

In a further aspect, a sensor system for detecting an analyte in an environment includes a sensor responsive to the analyte including a substrate and a sensor medium on the substrate. The sensor medium includes at least one nanostructure. At least one property of the sensor medium is dependent upon the presence of the at least one analyte. The nanostructure(s) of sensor hereof may be functionalized to increase the response thereof to the analyte. The sensor system further includes a dehumidifier system in fluid connection with the environment and with the sensor responsive to the analyte. The dehumidifier system includes at least one of (i) a condenser unit or (ii) a desiccant unit. The condenser unit may, for example, include a thermoelectric module having a cooling section and a heating section, wherein the cooling section is in fluid connection with an interior of a condensing chamber of the condenser unit. The condensing chamber further includes an inlet in fluid connection with the environment and an outlet in fluid connection with the sensor responsive to the analyte. The desiccant unit includes a desiccant material. The sensor system further includes electronic circuitry including at least one measurement system in operative connection with the sensor responsive to the analyte to measure a response of that sensor.

In a number of embodiments, the nanostructures include nanotubes, nanowires, nanofibers, nanorods, nanospheres, or mixtures thereof. The nanostructures may, for example, include or be formed from carbon, boron, boron nitride, carbon boron nitride, silicon, germanium, gallium nitride, zinc oxide, indium phosphide, molybdenum disulfide, or silver. In a number of embodiments, the nanostructures include carbon.

In a number of embodiments, the desiccant unit includes an inlet in fluid connection with an outlet of the condensing chamber and an outlet in fluid connection with the sensor responsive to the analyte. The desiccant material and a quantity of the desiccant material may, for example, be selected to limit removal of the at least one analyte for a given range of flow rate so that a sample reaching the sensor includes a concentration of analyte at or above the detection limit of the sensor. In a number of embodiments, the desiccant material includes calcium chloride.

The desiccant unit may, for example, include a volume of the desiccant material positioned in a conduit so that a sample from the environment must pass through the desiccant material. In a number of embodiments, the desiccant material is chosen so that the analyte elutes through the desiccant material before significant water elutes therethrough over a range of time. In a number of embodiments, measurement of the response of the sensor is timed to correspond with the range of time.

In a number of embodiments, the sensor medium includes a plurality of nanostructures in contact with titanium dioxide, and the sensor system further includes at least one energy source to apply electromagnetic radiation to the sensor medium for a period of time. The plurality of nanostructures may, for example, include carbon nanostructures. Titanium dioxide may, for example, be mixed with the nanostructures, immobilized upon the nanostructures, or covalently attached to the nanostructures. In a number of embodiments, titanium dioxide is deposited upon the nanostructures via sol-gel synthesis. In a number of embodiments, the plurality of nanostructures include a network of oxidized single-walled carbon nanotubes.

The measured response of the sensor may, for example, be an electrical property change or an optical property change. The substrate of the sensor may for example, include $SiO_2$ or a polymer.

The electromagnetic radiation source may, for example, be a source of UV light. A baseline for detection of the at least one analyte may, for example, be established (via the electronic circuitry) after application of the UV light for the period of time.

In a number of embodiments, the analyte is a component of breath (for example, human breath) which is more volatile that water. The analyte may, for example, be acetone, carbon dioxide, oxygen, hydrogen sulfide, nitric oxide, ethanol, isoprene, hydrogen, methane, or carbon monoxide. In a number of embodiments, the analyte is acetone.

In a number of representative embodiments, acetone sensors (for example, chemiresistors) fabricated from $SWCNT@TiO_2$ core-shell hybrid material hereof are capable of detecting acetone in the breath. The response of the sensor to dried breath samples linearly correlated to the concentration of BHB in the blood. Because of the cross sensitivity of the sensor to water vapor, a dehumidifier system with at least one of a condenser stage and a desiccant stage was used to dry the breath samples. In a number of embodiments, the dehumidifier system includes a condenser stage including at least one condenser unit in series with a desiccant stage including at least one desiccant unit. The dehumidifier system is placed between the environment to be sampled and the sensor(s) of the system. The implementation of the dehumidifier system significantly improved the calculated detection limit of the sensor as compared to measurements without dehumidification. When analyzing gases dried with the dehumidifier system, the calculated detection limit of acetone in a number of non-optimized sensor studies improved to approximately 1.3 ppm. To demonstrate the use case of the sensor in an acetone breathalyzer, a nanostructure-based chemiresistor was incorporated into a handheld breathalyzer device. The sensor response to breath samples corresponding to known concentration of BHB was shown to be linear. As ketogenic dieting and intermittent fasting become more widely adopted as protocols for treating a range of diseases, ketone tracking is important for achieving lasting dietary changes. The acetone sensors hereof may be used to easily monitor the ketosis state.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 8D illustrates schematically an embodiment of a voltage divider configuration of resistors for use in the electronic circuitry of the system of FIG. 8A, where a change in resistance is converted to a change in voltage.

FIG. 8E illustrates schematically an embodiment of a Wheatstone bridge for use in the electronic circuitry of the system of FIG. 8A.

FIG. 8F illustrates schematically an embodiment of electronic circuitry for use in connection with the system of FIG. 8A.

DESCRIPTION

Figure 1A:
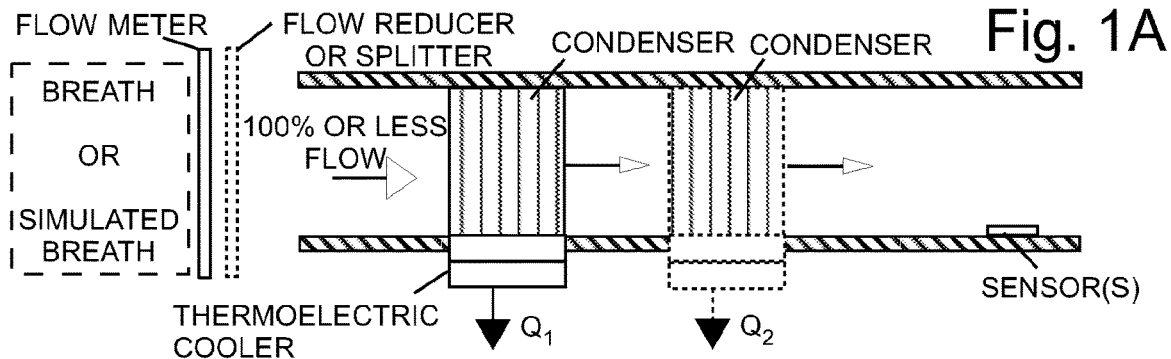
FIG. 1A illustrates schematically an embodiment of a sensor system hereof including one or more condensers for dehumidification, wherein Q indicates heat removal from the hot side of the thermoelectric cooler of the condenser(s).

The present devices, systems, methods, and compositions, along with the attributes and attendant advantages thereof, will best be appreciated and understood in view of the following description taken in conjunction with any accompanying drawings.

In a number of embodiments, devices, systems, and methods hereof provide for improved performance (for example, improved sensitivity) of a sensor to an analyte or target composition by decreasing the humidity of a sample flow from an environment to the sensor. In a number of embodiments, the sample flow is from exhaled breath. In that regard, it has been discovered that the sensitivity of various sensors (for example, sensors including a sensor medium including one or more nanostructures) may be improved if humidity/water vapor content in a gaseous environmental sample is decreased. Such a decrease in humidity may, for example, be particularly advantageous in the case that the environmental sample includes exhaled breath. Exhaled breath is typically saturated (100% relative humidity) or very nearly saturated with water vapor. The analyte may, for example, be a component of human exhaled breath that is more volatile (that is, has a boiling point less than) water (for example, volatile organic components and various inorganic and elemental gases found in breath). Many such volatile components of breath are described in Costello, B. D., et al., "A Review of the Volatiles from the Heathy Human Body," *J. Breath Res.*, 8, (2014), the disclosure of which is incorporated herein by reference.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etcetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a dehumidifier" includes a plurality of such dehumidifiers and equivalents thereof known to those skilled in the art, and so forth, and reference to "the dehumidifier" is a reference to one or more such dehumidifiers and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

Electronic circuitry (for example, including a power supply, a processor systems, a memory system, user interface devices, etc.) may be used in control and measurement in sensor systems and methods hereof. The terms "electronic circuitry", "circuitry" or "circuit," as used herein include, but is not limited to, hardware, firmware, software, or combinations of each to perform a function(s) or an action (s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software. As used herein, the term "logic" is considered synonymous with the term "circuit."

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

A thermoelectric module (sometimes referred to as a Peltier module) is a device that creates a heat flux at a junction of two different types of materials using the Peltier effect. A thermoelectric or Peltier module may, for example, include semiconductor pellets and ceramic substrates. As the pellet carriers are charged via, for example a DC power supply, they release heat from one substrate (the "hot/ heating section" or "hot side"). The other side of the thermoelectric module (the "cold/cooling section" or "cold side") absorbs heat. A typical thermoelectric module may, for example, include two ceramic substrates sandwiching many pairs, or "couples" of, for example, bismuth telluride pellets or dice. The (pairs of) pellets may be connected electrically in series, and thermally in parallel, between the ceramics. As described above, one of the ceramics will be the "hot/heating section" or "hot side" and the other will be the "cold/cooling section" or "cold side." In a number of embodiments hereof, the cold/cooling section or cold side of a thermoelectric module (or Peltier module) is used in dehumidifying a sample by condensing moisture in the sample flow.

A system used to study removal of water vapor/humidity from a flow stream via one or more dehumidifier units, devices of systems (dehumidifiers) is illustrated schematically in FIG. 1A. A first part or portion of the system is positioned before a flow meter and simulates human breath flow rate and relative humidity by creating a flow of moisturized air. According to research studies, the human exhalation rate is between 6 liter per minute to 9 liter per minute or 13.13 cubic feet per hour to 19.07 cubic feet per hour. The relative humidity of human exhaled breath is 100%. A system or device may also be provided to reduce the amount of flow exiting the first part or portion of the system. The second part of the illustrated embodiment of the system of FIG. 1A includes one or more dehumidifiers (condensers or condenser units in FIG. 1A) including thermoelectric modules in series.

Figure 1B:
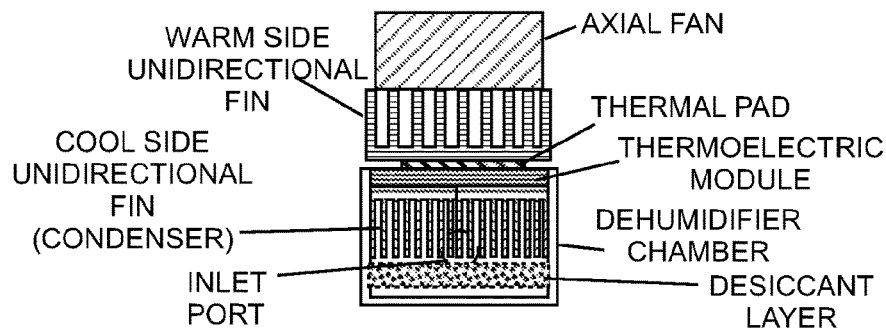
FIG. 1B illustrates schematically an embodiment of a condenser for use in the sensor system of FIG. 1A.
Figure 1C:
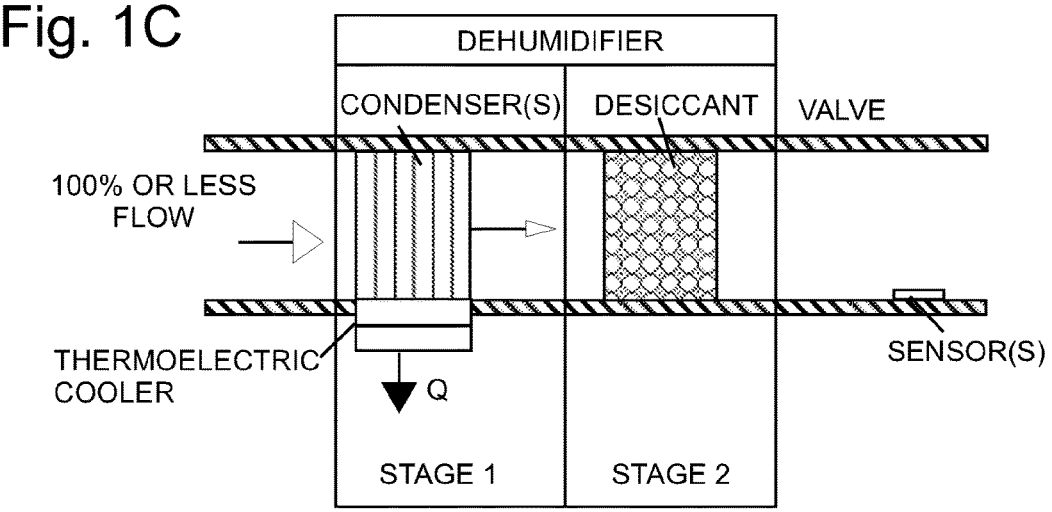
FIG. 1C illustrates schematically an embodiment of a system hereof including a multistage dehumidifier or dehumidification section including a first stage including one or more condenser units and a second stage including one or more desiccant units.

In various studies, a source of water vapor (for example, aquarium bubbler etc.) was used to moisturize air in the sample delivered to the systems of FIGS. 1A and 1C. In a number of studies, a DHT22 humidity sensor available from Adafruit was used to measure humidity. A flowmeter such as a Dwyer air flowmeter having a range from 0 to 20 square feet per hour was used to measure flow. In formulating high humidity air, water may, for example, be vaporized into fine water droplets or a fog-like mist. Air flow rate could be adjusted via an adjustable pump system.

In a number of embodiments, a thermoelectric or Peltier module having a size of 40 mm×40 mm was used in a dehumidifying condenser hereof. FIG. 1B illustrates schematically a dehumidifier hereof which includes an axial fan, hot-side and cold-side heatsinks (for example, including extending fins with intermediate ducts), a thermoelectric or Peltier module and a dehumidifier chamber (formed, for example, from an acrylic polymer). In general, the term "heatsink" as used herein refers to passive heat exchangers that are designed to increase or maximize the surface area in contact with medium to/from which energy is to be exchanged. As described above, a thermoelectric or Peltier module has both a hot/heating section, surface or side and cold/cooling section, surface, or side. When DC voltage is applied to the module, heat energy released via the hot side substrates is dissipated by external convection. Since the module size was only 40 mm×40 mm, an omnidirectional heatsink including a plurality of spaced fins was attached to the hot side of the module to increase surface area. An axial fan was positioned on top of the heatsink to facilitate removing heat. On the opposite side or cold side of the ceramic substrate, heat is absorbed from the surrounding volume. To increase thermal conductivity thermal interface materials like thermal pads or thermal greases may be used to smooth thermal resistance difference between a heatsink and each of the hot side and/or the cold side of the thermoelectric module. An omnidirectional heatsink including a plurality of spaced fins was also applied to the cold side to increase surface area. In a number of studies, the thermoelectric module and the cold-side heatsink were placed inside a clear acrylic (condensing) chamber with one inlet and one outlet port (not shown in FIG. 1B) for a dehumidifying process associated with collecting condensed water as shown in FIG. 1B.

Figure 1D:
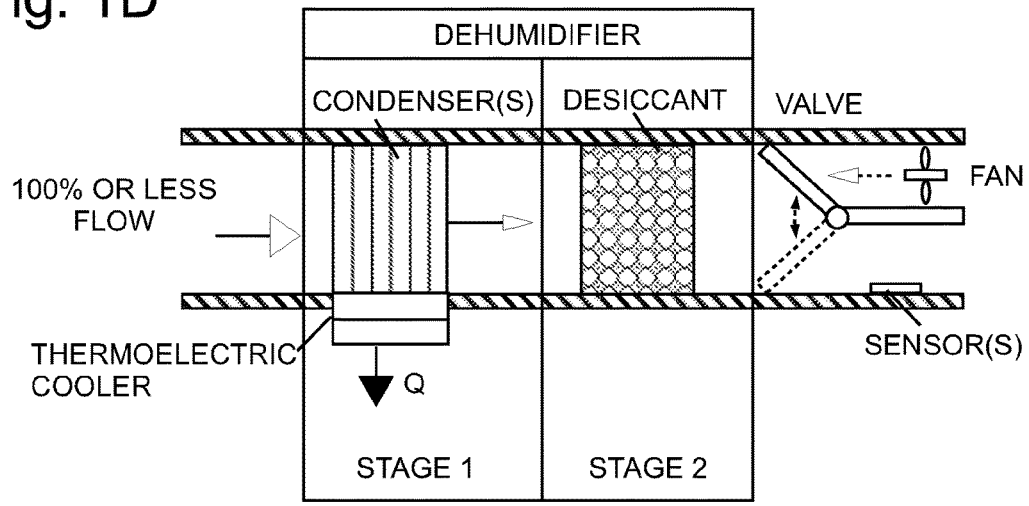
FIG. 1D illustrates schematically another embodiment of a system hereof including multistage dehumidifier or dehumidification section including a first stage including one or more condenser units, a second stage including one or more desiccant units and a system for drying the dehumidification section.

As illustrates in broken lines in FIG. 1A, to enhance dehumidifier function, one can place another dehumidifier unit or condenser in the system to form a multi-stage dehumidifier. Additionally or alternatively a desiccant layer may be added within the condenser chamber as illustrated in FIG. 1B. Moreover, one may add a second stage including a desiccant dehumidifier, independent of any condenser, in series with a first stage including a condenser as illustrated in FIGS. 1C and 1D. In a number of embodiments, a desiccant unit was placed in series with and after one or more condenser units.

In a number of studies, two condenser units including thermoelectric modules were placed in series connection as illustrated in FIG. 1A. Humidity results were obtained by measuring humidity of the flow from the system, once that flow exits the system outlet. For human breath simulation in the first portion of the system of FIG. 1A in which simulated breath is created, the relative humidity percentage reached 91 percent at a 13 cubic feet per hour flow rate. If one raises the air pump power to increase flow rate to 19 cubic feet per hour, the relative humidity could still reach around 85 percent. In the second or dehumidifier/condenser part or portion of the system of FIG. 1A, a single-stage dehumidifier without a desiccant layer reduced the humidity to 17 percent, which is a good result for only a single, non-optimized condensing process. After adding desiccant layer to the dehumidifying chamber of the single-stage system one could reduce the humidity to 14 percent. A multi-stage embodiment including two condensers as dehumidifiers was also studied. With the condenser unit dehumidifiers connected in parallel, the humidity remained the same as single-stage design, but one can dehumidify higher flow rates over the same time. On the other hand, if the condenser unit dehumidifiers are connected in series, the multi-stage dehumidifier can reduce humidity to below 10 percent (for example, to 8.4 percent in a number of studies). Dehumidifier systems hereof were further studied and optimized in the study of representative nanostructure-based acetone sensor as described below. Although nanostructure-based acetone sensors are used in representative studies, one skilled in the art appreciated that dehumidifier systems hereof are suitable for use in connection with other sensors and in a variety of other uses.

The reduction of humidity to 10 percent or less is, for example, desirable in a nanostructure-based acetone sensor as described in U.S. Pat. No. 10,244,964, the disclosure of which is incorporated herein by reference, which describes a sensor including titanium dioxide on single-walled carbon nanotubes (SWCNT@$TiO_2$) in several embodiments thereof. As described in U.S. Pat. No. 10,244,964, a number of strategies may be used to functionalize electrically conductive nanostructures such as single-walled carbon nanotubes (SWNTs or SWNCTs) with titanium dioxide ($TiO_2$) nanostructures for the development of, for example, acetone sensors.

Singled-walled carbon nanotubes or SWCNT are a class of gas sensing material with a promising potential for sensors including those for breath analysis. Because of their high surface to volume ratio, SWCNT are effective transducers as gas sensors. They are sensitive to small concentrations of gaseous analytes and are capable of detecting small changes in electrical charges around their local environment. Combining the SWCNT with receptor groups such as polymers, biomolecules, nanoparticles, or organometallic compounds is a well-tested strategy to selectively detect analytes down to the ppb level. U.S. Pat. No. 10,244,964 demonstrated acetone detection using titanium-dioxide-functionalized SWCNT (SWCNT@$TiO_2$) based chemiresistors and other receptor functionalized SWCNT. Such functionalization strategies improved the sensitivity to acetone compared to bare SWCNT alone.

Various nanostructures other than SWCNT are suitable for use in nanostructure-based sensors which include, for example, multi-walled nanotubes, nanowires, nanofibers, nanorods, nanospheres, or the like, or mixtures of such nanostructures. Moreover, in addition to carbon, those skilled in the art will appreciate that the nanostructures for acetone and/or other sensors can be formed of boron, boron nitride, and carbon boron nitride, silicon, germanium, gallium nitride, zinc oxide, indium phosphide, molybdenum disulfide, silver, and/or other suitable materials.

Figure 2:
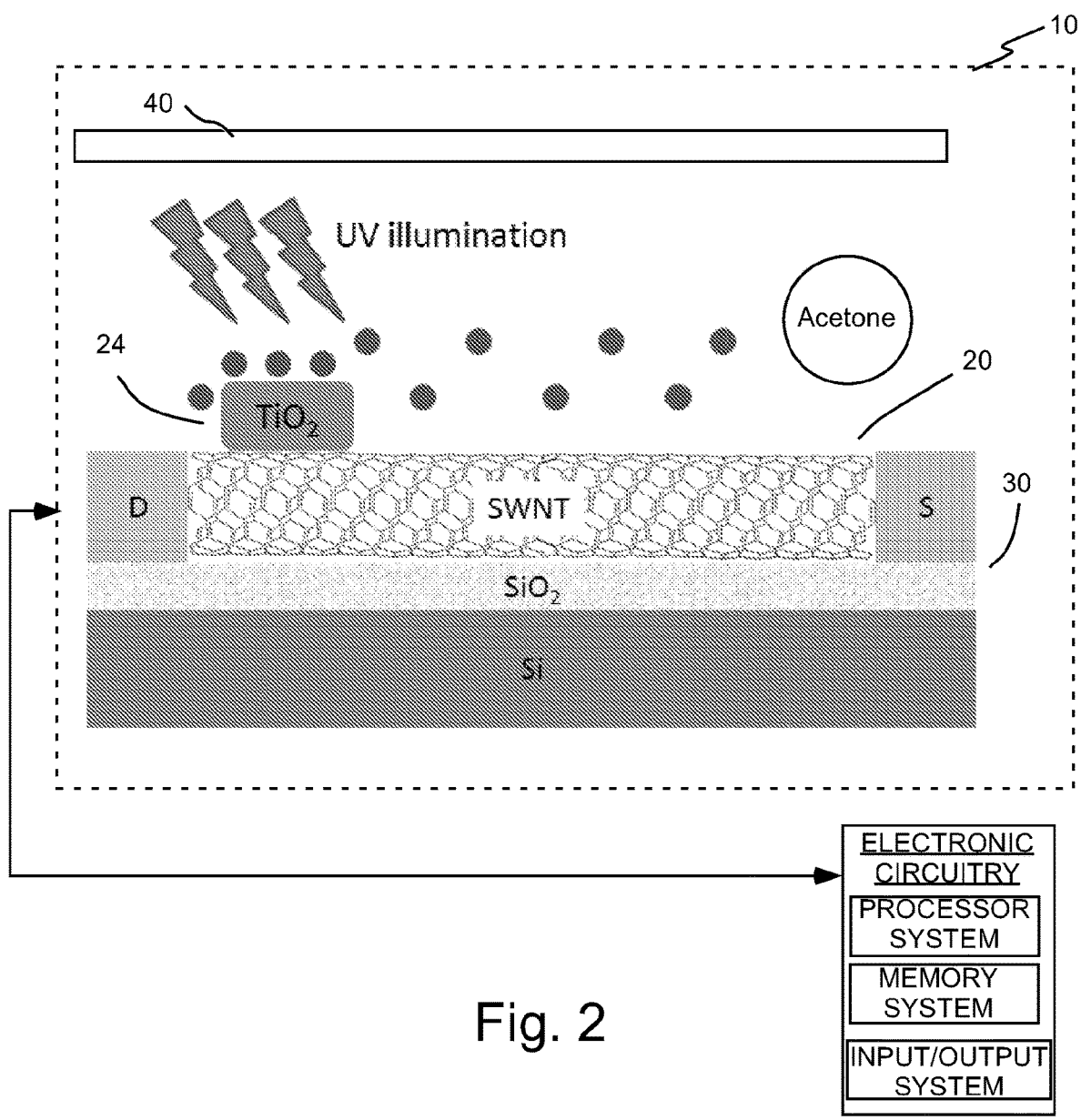
FIG. 2 illustrates schematically an embodiment of an acetone sensor device or system hereof.

As illustrated in FIG. 2, a semiconducting SWNT or network of SWNTs 20 (or other nanostructures) can, for example, be disposed upon a substrate 30 (for example, $SiO_2$) and contacted by two conductive (for example, metallic such as Au and/or Ti) electrodes representing a source (S) and a drain (D). In a number of embodiments, a $TiO_2$ layer 24 is be provided in connection with the SWNT network 20. In the SWNT@$TiO_2$ hybrid structure of FIG. 2, SWNTs were used as electrical signal transducer and $TiO_2$ was used as an acetone receptor or recognition layer.

In single-walled carbon nanotubes, all carbon atoms are located on the surface where current flows, making a stable conduction channel that is extremely sensitive to a surrounding chemical environment. As described above, nanotubes, including SWNT's, have the ability to change conductance in response to interaction with (for example, absorption of) different gases. This characteristic is, for example, implemented in system 10. In the embodiment illustrated, electromagnetic energy (for example, UV light such as light having wavelengths of 288 nm and 375 nm) is transmitted from an energy source 40 from above. Energy can additionally or alternatively be transmitted through an optically transparent support (for example, an optically transparent quartz support) from below. Application of electromagnetic energy such as UV energy to a structure including nanostructures and titanium dioxide before the structure is exposed to a gas sample from an environment to be tested has been found to substantially improve lower limits of detection of an analyte such as acetone.

Acetone is a metabolic byproduct found in the exhaled breath and can be measured to monitor the metabolic degree of ketosis. In this state, the body uses free fatty acids as its main source of fuel because there is limited access to glucose. Monitoring ketosis is important for type I diabetes patients to prevent ketoacidosis, a potentially fatal condition, and individuals adjusting to a low carbohydrate diet.

Figure 3:
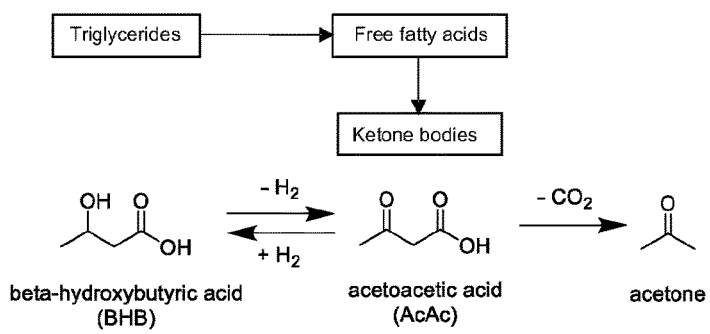
FIG. 3 illustrates the metabolic processes that produce ketone bodies.

Acetone in the breath is an indication of the body being in a state of ketosis. The liver breaks down fatty acids into ketone bodies, which are acetone, acetoacetate (AcAc), and beta-hydroxybutyric acid (BHB), and then releases them into the blood stream (see FIG. 3). Cells uptake AcAc and BHB and converts them into acetyl-CoA to use as part of the citric acid cycle in the mitochondria to produce ATP, while acetone is mostly disposed as a byproduct. The high volatility of acetone results in ppm concentrations of acetone found in the human breath.

As set forth above, acetone is a biomarker for a metabolic process known as ketosis. Ketosis occurs when the body is deprived of glucose through dietary changes, and also when glucose and ketone body production by the liver are rapid in the absence of insulin. Ketosis may be harmful or beneficial depending on the patient group. Type I diabetics with severe insulin deficiency, typically presenting in childhood, risk facing an uncontrolled ketone production and dehydration leading to diabetic ketoacidosis. This condition is caused by the low pKa of the AcAc (3.58) and BHB (4.70) acidifying the blood and may lead to a coma and even death. However, for certain patient groups with type II diabetes, drug resistant epilepsy and other neurological diseases, ketosis may be purposefully induced through dietary changes for therapeutic benefits. Nutritional ketosis, defined as BHB range between 0.5 to 3.0 mM, may be achieved by consuming a high-fat, low-carbohydrate ketogenic diet or intermittently fasting for several days at a time. Monitoring the concentration of ketones may, for example, be useful for preventing ketoacidosis, or for helping make informed dietary adjustments to achieve therapeutic levels of ketones.

Breath testing is a promising new sampling method to monitor ketosis. In research and clinical labs, quantitative breath tests are done using a proton-transfer-reaction mass spectrometry (PTR-MS) or secondary ion mass spectrometry (SIMS). These instruments are too large and expensive to be used at the point of care and require trained personnel. An acetone sensor incorporated into a breathalyzer is a simpler tool to easily monitor ketosis. Rapid quantification of breath acetone has the potential to be a powerful feedback tool for improving health outcomes. A desirable acetone breath sensor is sensitive to acetone in the range of approximately 1 to 1,000 ppm (which corresponds to a ketosis state ranging from overnight fasting to ketoacidosis) and is significantly more selective toward acetone over both endogenous and exogenous compounds found in the breath such as water vapor, carbon dioxide, ammonia, isoprene, and ethanol. A majority of the acetone sensors developed in the past decade have been based on nanostructures of semiconducting metal oxides. Tungsten oxide based sensors have especially received the most research interest including human breath studies to monitor ketosis.

A significant issue with quantifying acetone concentration in the breath using a SWCNT@$TiO_2$ material is cross sensitivity to water vapor. Cross sensitivity of SWCNT-based devices to humidity is a recurring problem that has hindered the adoption of SWCNT-based sensors for many real world sensing applications. In a number of studies hereof, it is demonstrated that a dehumidifier system including a condenser stage (including one or more condensers or condenser units) and/or a desiccant stage incorporated inline with an acetone sensor (as illustrated, for example, in FIGS. 1A and 1C) can reduce the humidity content of both breath mimics and human breath samples below 1% RH (which was the RH sensor detection limit) to detect acetone. The dehumidifier/condenser effectively functions as a cold trap to remove water vapor from gas samples. The devices, systems and methods hereof further advance many possible applications for SWCNT gas sensors. For example, such sensors may be used as a breath acetone sensor to replace the more difficult urine and blood sampling methods commonly used to monitor ketosis.

Figure 4:
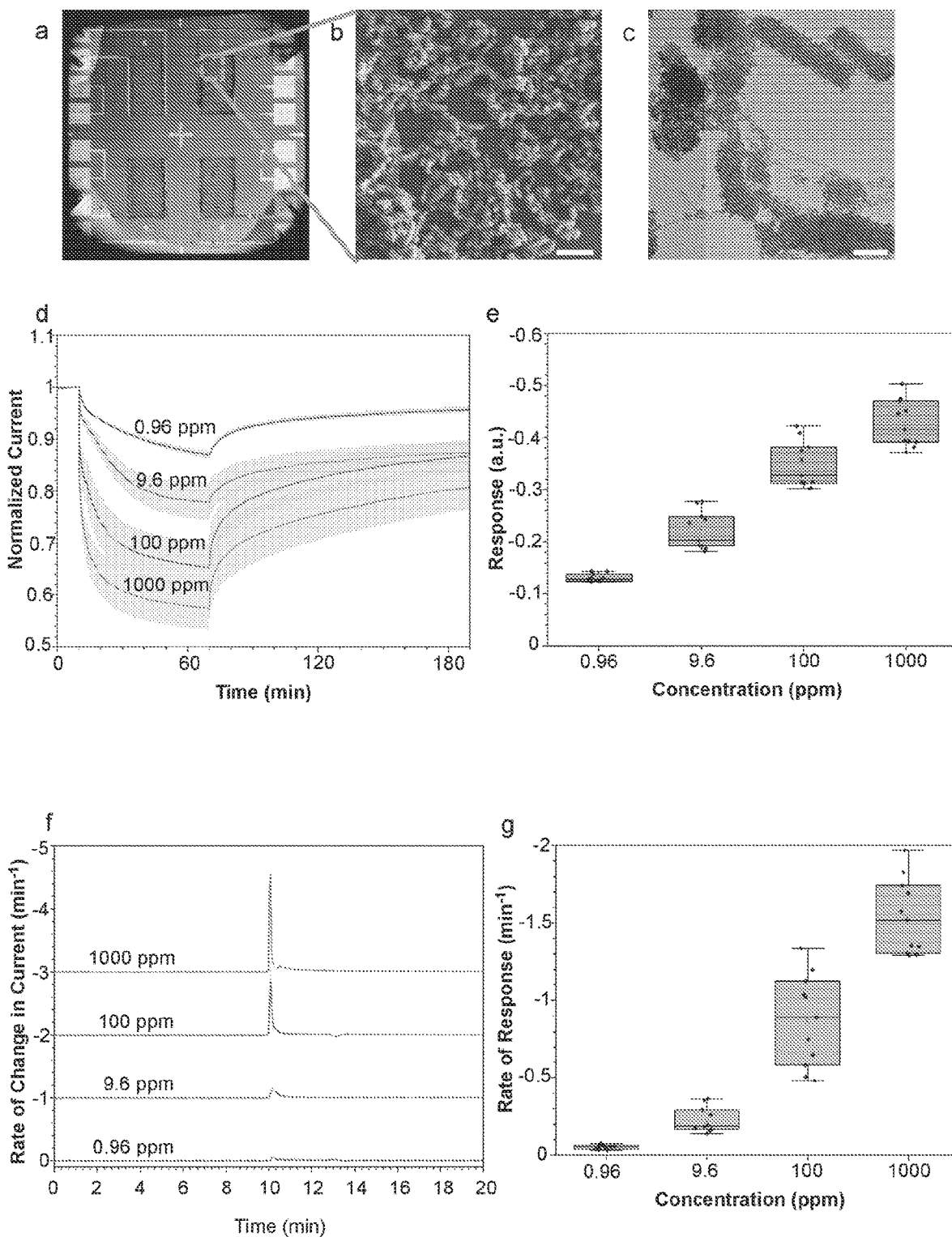
FIG. 4 illustrates characterization of acetone sensors hereof, wherein: panel (a) illustrates an optical image of a 2×2 mm silicon die with SWCNT@TiO$_2$ deposited on 4 pairs of interdigitated gold electrodes and wherein each pair of the electrodes is considered a chemiresistor device; panel (b) illustrates an SEM image of the SWCNT@TiO$_2$ deposited on a gold electrode (Scale bar=1 μm); panel (c) illustrates a TEM image of the SWCNT@TiO$_2$ (Scale bar=100 nm); panel (d) illustrates response and recovery traces of 11 devices to 0.96, 9.6, 100, and 1,000 ppm of acetone, wherein the shading marks one standard deviation; panel (e) illustrates response calibration of the sensor traces; panel (f) illustrates the first derivative of the sensor traces zoomed in around the response region; and panel (g) illustrates a box plot of concentration dependent maximum rate of change.

Packaged silicon dies with deposited SWCNT@$TiO_2$ (FIG. 4, panels a-c) were formed as described in the Experimental Examples section hereof and tested for sensitivity to acetone by exposing the sensor to 0.96, 9.6, 100, and 1,000 ppm of acetone. For each exposure, 10 minutes of background current was collected, followed by 60 minutes of exposure to acetone to collect the response curve, and then followed by 120 minutes of purging with the carrier gas to collect the recovery trace (FIG. 4, panel d). The calculation for sensor response is set forth in Experimental Examples section hereof.

The maximum response after the 60 minutes of acetone exposure followed a logarithmic relationship to the acetone concentration (FIG. 4, panel e). Without limitation to any mechanism, the large device-to-device variation was likely caused by the heterogeneity of $TiO_2$ functionalization on the SWCNT and other common causes of SWCNT device-to-device variability such as nanotube bundling, charged states on the $SiO_2$ substrate, presence of both metallic and semiconducting nanotubes, and inconsistent formation of the nanotube network. However, clustering of devices was observed, and low variance selection criteria could be applied to improve the device-to-device variability albeit at a lower device yield. The variance, as quantified as interquartile range, was reduced from 0.0787 to 0.0135 for sensor response to 1,000 ppm of acetone by selecting 4 out of the 11 devices. Inkjet printing methods as known in the art may, for example, be implemented to fabricate larger quantities and higher yields of chemiresistors with lower device-to-device variability.

Even after 60 minutes of exposure to acetone, the sensor response did not fully reach steady state as the normalized current continued to drift to lower values. The slow response was especially pronounced for the lowest concentration of acetone 0.96 ppm. The sensor response time as calculated as the time it took to the signal to reach 90% of the maximum response were on the order of tens of minutes. Even after two hours of purging with air, the sensors did not completely recover to their initial conductivity indicating a combination of chemisorption and physisorption of acetone was occurring on the $TiO_2$ surface.

For applications in breath acetone monitoring, it is desirable that the sensor generate a robust signal within a time frame corresponding to a slowly exhaled breath (<1 minute). To determine the rate of response of the sensor to acetone, the first derivative of the sensor trace was calculated and plotted (FIG. 4, panel f). The rate of change in the sensor conductivity was largest approximately 10 seconds after introduction of acetone and started to completely level off after just two minutes of exposure. This sharp drop off in the rate of response indicated that the largest changes in the sensor conductivity had occurred within minutes of acetone exposure and a longer exposure is not necessary to generate a sensor signal. FIG. 4, panel g sets forth a box plot of concentration dependent maximum rate of change.

Figure 5A:
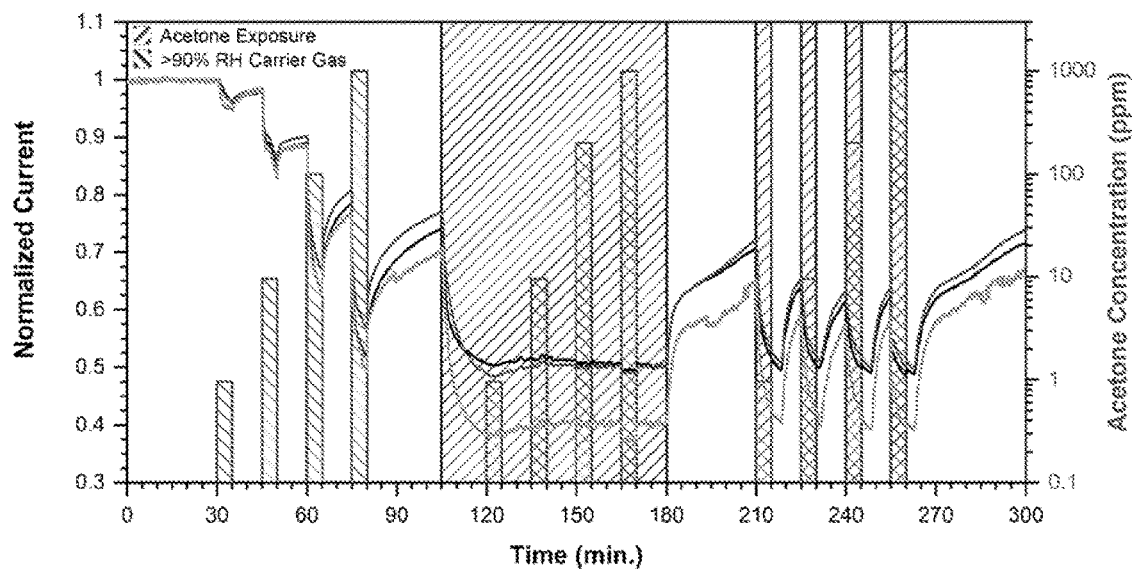
FIG. 5A illustrates normalized current traces of three representative acetone chemiresistor devices exposed to 5-minute pulses of dried acetone vapor, pulses of acetone vapor in constant background humidity, and pulses of acetone and humidity.
Figure 5B:
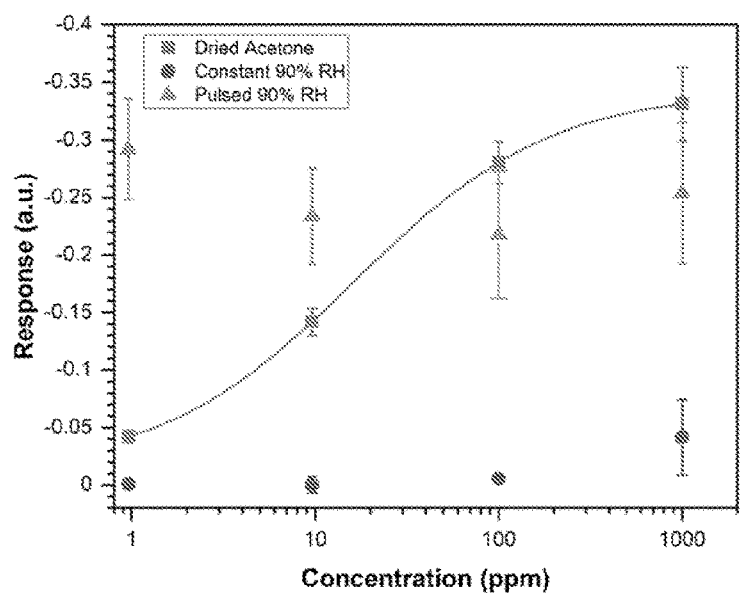
FIG. 5B illustrates calibration curves of the sensor traces in FIG. 5A.

As described above, a major component of an exhaled breath is water vapor. To study humidity cross-sensitivity of the acetone chemiresistor sensors hereof, the acetone chemiresistors were exposed to 0.96, 9.6, 100, and 1,000 ppm of acetone in dry air followed by humidified air (FIG. 5A). Three representative devices were selected for detailed acetone sensing studies based on their low device-to-device variability. Their average response to 9.6 ppm of acetone in dried air was −0.1417±0.0116 (relative standard deviation (RSD)=8.12%) (FIG. 5B). Additionally, a single device was shown to have consistent response to 9.6 ppm of acetone from day-to-day, −0.0567±0.0037 (RSD=6.53%) if the device was hydrated by soaking the deposited material in deionized (DI) water right before testing. This reusability allowed the same set of devices to be used for multiple different studies. Permitting the deposited SWCNT@$TiO_2$ material to dry out decreased the sensitivity to acetone over time, indicating (without limitation to any mechanism) that water molecules play an important role in the sensing mechanism through a competitively binding process. As set forth above, to retain the sensitivity to acetone, the sensor material should be hydrated before use. Sensors can be hydrated or a breathalyzer system that uses a new sensor for each measurement can be used. The new sensor can, for example, come prepackaged in a sealed humid container before it is inserted into the breathalyzer system.

In dry air, the SWCNT@$TiO_2$ devices had a calculated detection limit of 0.1 ppm of acetone (using S/N=3). Under constant background humidity (>90% RH), the response to humidity overwhelmed the sensor. Only the response to 1,000 ppm of acetone could be observed in the sensor traces. Response to 100 ppm could not be resolved above the noise level. This detection limit is well above the 10 ppm of acetone that is required to monitor ketosis. In a more realistic simulation that mimicked the exhalation of the human breath, a pulse of humidified air containing acetone was applied to the sensor. The humidity in this case oversaturated the sensor to the point where even the 1,000 ppm of acetone could not be resolved.

Figure 5C:
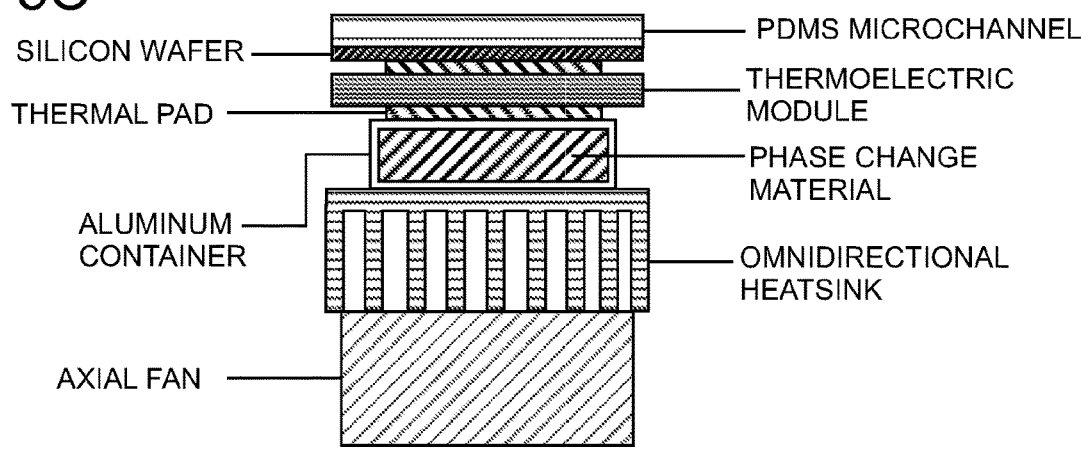
FIG. 5C illustrates schematically an embodiment of a condenser or condenser unit hereof including microchannels within the condenser chamber thereof.

To reduce the humidity cross-sensitivity issue and to be able to measure acetone in the human breath, a dehumidifier was designed and prototyped which was similar to that illustrated FIG. 1C. The dehumidifier was made up of two main stages, a condenser fabricated from thermoelectric cooled microchannels (FIGS. 5C and 5D) powered at a voltage of 6 V and a calcium desiccant plug (FIG. 5E) with a length of 5 cm. The efficacy of the dehumidifier was tested by comparing the humidity level of a humidified gas stream before and after drying. Although the dehumidifier did not completely dry out the gas stream, it was able to slow the rate of water vapor breaking through to the sensor. The humidity level was reduced from 95.0% to 27.4% RH for a gas stream flowing for 5 minutes at 200 sccm.

The volume or mass flow rate of sample delivered to the dehumidifier systems and sensor(s) hereof may be decreased to facilitate reduction of humidity to a desired, predetermined level. As illustrated, for example, in FIG. 1A, a system hereof may include a flow reducer or splitter that decreases flow from an environmental sample to be tested (for example, human breath) to less than 100% of the original flow. The amount of flow delivered to the dehumidifier system/sensor(s) is readily determined based upon the predicted humidity in the original sample, the capacity of the units of the dehumidifier system, the response characteristics sensor(s), etc.

Figure 5D:
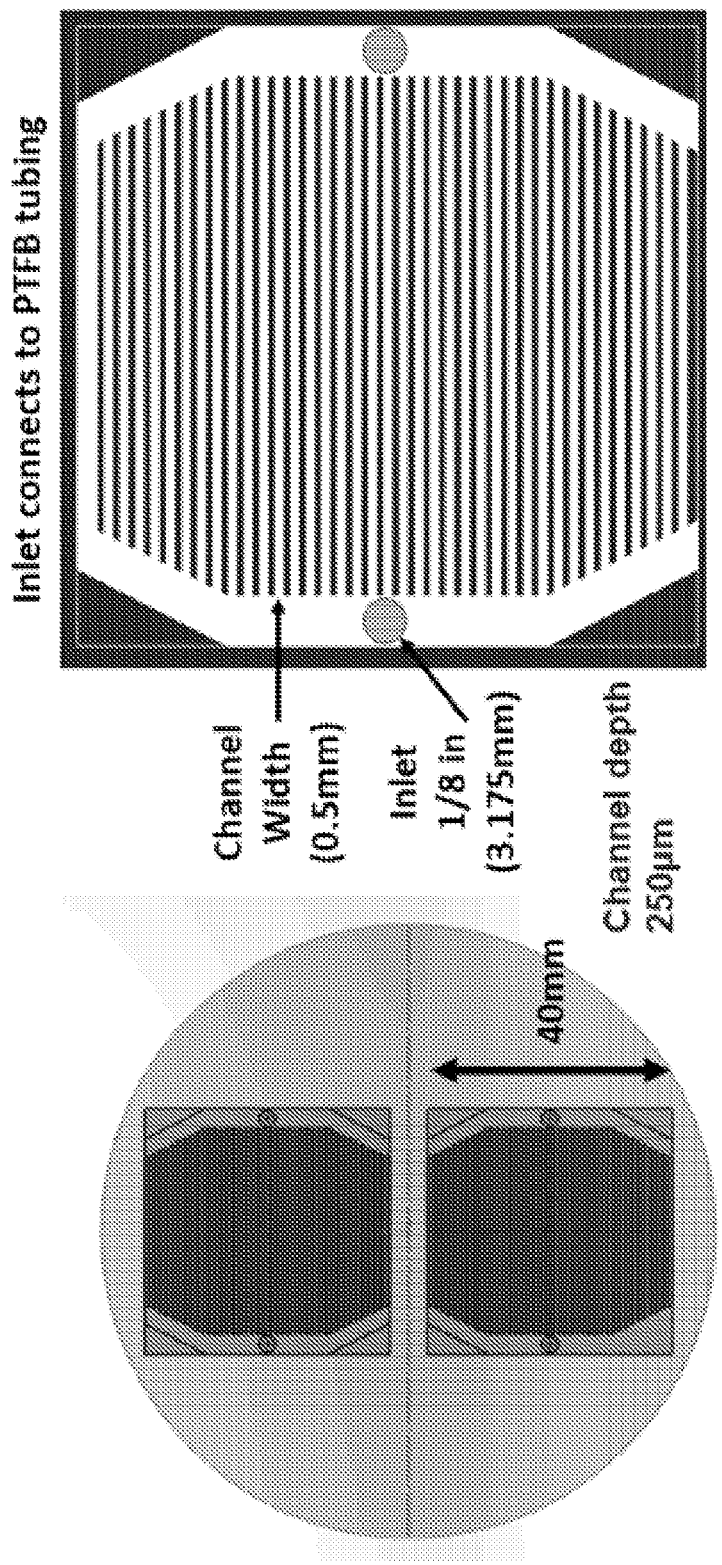
FIG. 5D illustrates schematically the condenser chamber and the microchannels of the condenser of FIG. 5C.

Use of a microchannel-based condenser assist in reducing the size of dehumidification systems hereof (for example, for use in handheld or portable sensing systems). Microchannel-based heatsinks may, for example, provide for efficient heat transfer between a sample having a relatively low flow rate and the heatsink by maintaining relatively high interfacial surface area. In such a condenser, the cool-side heat sink can, for example, include a plurality of spaced plates, fins or extensions which define microchannels therebetween. In general, microchannels suitable for use herein have a hydraulic diameter no greater than 5 mm or no greater than 1 mm. In a number of embodiments, the hydraulic diameter of the microchannels is in the range of 1 µm to 5 mm or within the range of 1 µm to 1 mm and the channel depth is in the range of 1 µm to 5 mm or in the range of 1 µm to 1 mm. In the embodiment of FIG. 5D, the channel width is 0.5 mm and the channel depth is 250 µm.

The dehumidifier systems can be further miniaturized to, for example, be incorporated into the breathalyzer system (see, for example, FIG. 8A) and be further optimized to deliver dried acetone to the sensor within 30 seconds of breath exhalation. By, for example, decreasing the amount of breath sample that needs to be applied to the sensor to see a signal, the dehumidifier system can be significantly miniaturized. In that regard, only a portion of an exhaled breath (or other) sample can be delivered to the systems hereof for analysis in a number of embodiments.

Figure 5E:
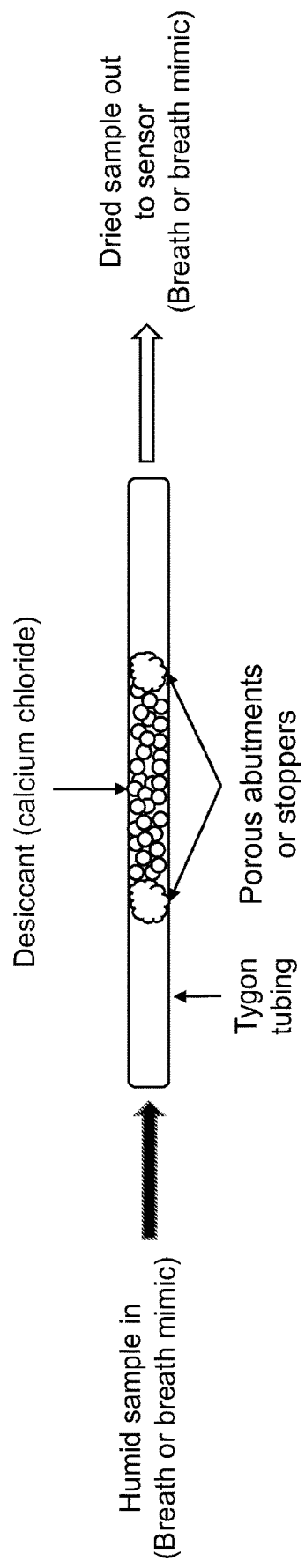
FIG. 5E illustrates schematically an embodiment of a desiccant system for used in the systems hereof.

FIG. 5E illustrates an embodiment of a dehumidifier unit, system or stage including a desiccant in which a segment of, for example, TYGON® tubing (a flexible polymer tubing available from Saint-Gobain North America of Malvern, Pennsylvania, which may, for example, having an inner diameter: 5/16 in. and an outer diameter: 7/16 in.) is packed with, for example, approximately 1.25 inches (approximately 0.78 g) of granular calcium chloride. In a number of studies, the mass of calcium chloride was retained within the tube via flow-through or porous abutments or stoppers on each side thereof. In the embodiment illustrated in FIG. 5D, each side of the calcium chloride was blocked with, for example, 1/8 in. pieces of cotton to prevent the desiccant from spilling out. In a number of studies, an additional piece of cotton was placed near the inlet of the desiccant system to absorb water as a precautionary step but wetting of that piece of cotton was not observed.

One should choose a desiccant for used in the devices, systems, and methods hereof that exhibits only limited or no adsorption of the analyte over the flow rate range of the sensor system. A number of desiccants such as commonly used silica gels were found to be unsuitable for use in connection with a sensor for acetone. In that regard, other desiccants and dehumidification methods were tested. Compared to calcium chloride, desiccants such as calcium oxide, sodium polyacrylate, silica and 3 Å molecular sieve, either failed to sufficiently dry the gas stream or absorbed significant amounts of acetone (silica gel and molecular sieves) in the flow rate range of the devices, systems, and methods hereof. Polymer thin films applied above the sensor to block out the humidity were also found to be ineffective. Such polymer thin films either did not allow any acetone to pass through or failed to keep the water vapor from reaching the sensor.

The rate at which humidity can break through the desiccant layer or mass is dependent on the flow rate of the sample gas stream. To minimize the rate of water vapor breaking through the desiccant, humid gas samples may be processed at a lower flow rate. The response of the acetone sensors hereof to, for example, 100 ppm of acetone was found to be dependent on the flow rate (sccm=standard cubic centimeters per minute) at which the acetone is flowed through the desiccant and delivered to the sensor. Since the calcium chloride absorbs some acetone, the sensor responds more quickly and at a larger magnitude to the same concentration of acetone at higher flow rates. The identity and mass of desiccant used, and the sample flow rate may thus be readily optimized for humidity reduction and sensor response for a particular analyte and sensor therefor via routine studies and knowledge in the art. The desiccant material and the quantity of the desiccant material may, for example, be selected to limit removal of the at least one analyte (via the desiccant) for a given range of flow rate or range of flow rates so that the sample reaching the sensor includes a concentration of analyte at or above the detection limit of the sensor.

In a number of aspects, the desiccant systems hereof, which may include a mass or column of desiccant material disposed within a conduit through which the sample passes, operate in the manner of an absorption column. Eventually, breakthrough of water may occur in the desiccant system. In a number of embodiments, the desiccant material may be chosen such that the analyte elutes from the column of desiccant material before water. The desiccant chosen will depend upon the physiochemical characteristics of the analyte and of the desiccant material but is readily determinable using the methodologies disclosed herein, well-known engineering principles and knowledge from the literature. Likewise, the sample flow rate and volume of desiccant are readily determinable/optimizable. In cases, in which breakthrough occurs (depending upon the capacity of the desiccant material for a given sample flow rate), there may be a temporal aspect to the measurement of the analyte. In that regard, the measure of the response to the sensor may be timed to occur in a range of time wherein the analyte has eluted form or passed through the desiccant material but water has not to a significant degree (for example, so that the sample reaching the sensor includes a concentration of analyte at or above the detection limit of the sensor without significant interference from water vapor). The measure may, for example, be timed so that sample humidity is below a predetermined threshold level during the measurement.

Figure 5F:
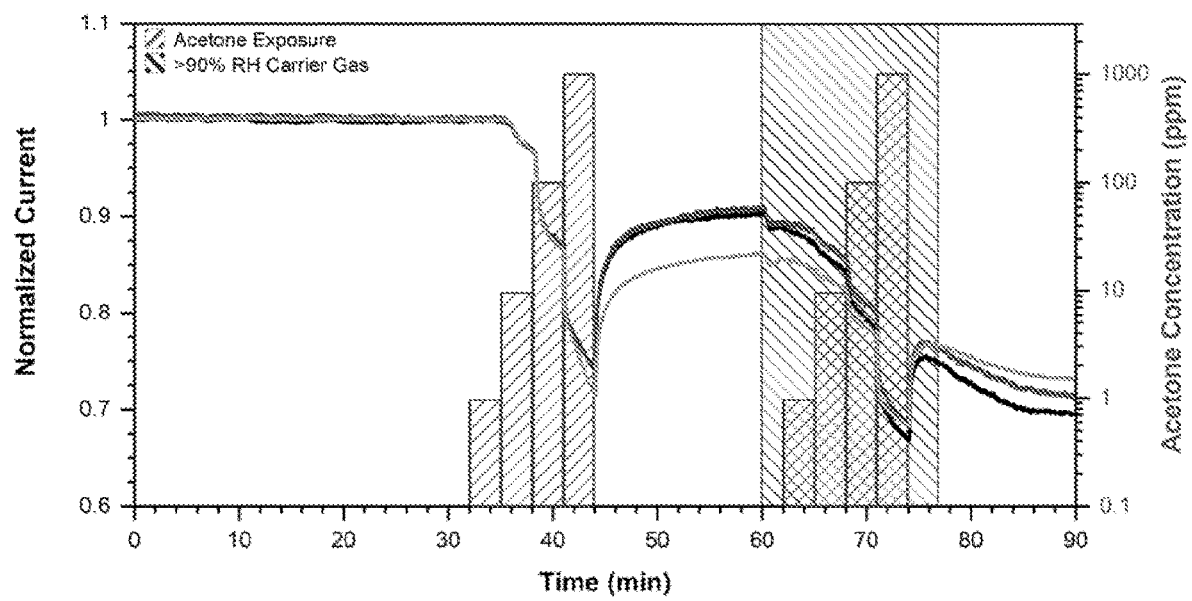
FIG. 5F illustrates normalized current traces of chemiresistor devices hereof that had been exposed to dried and humidified gas streams processed through the dehumidifier system.
Figure 5G:
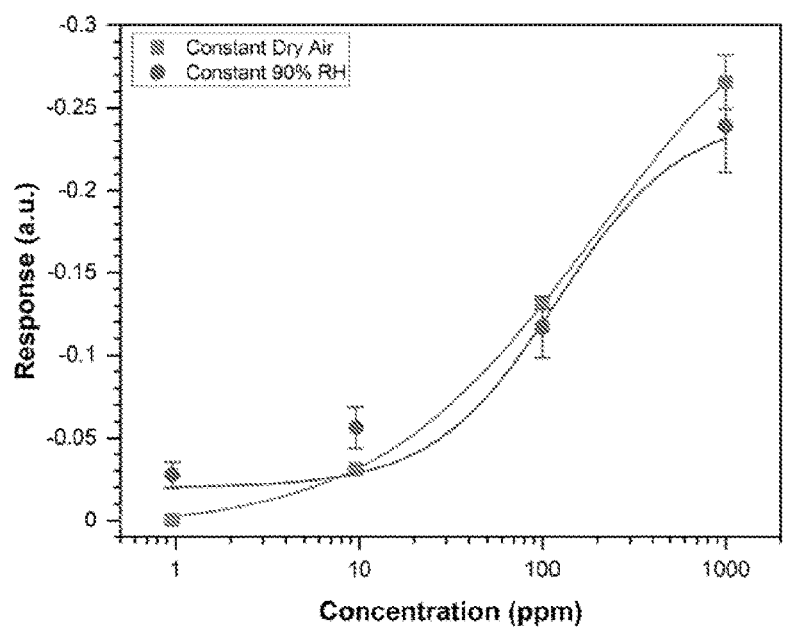
FIG. 5G illustrates calibration curve of the sensor traces in FIG. 5F.

An issue that prevented the continuous use of the dehumidifier in several studies was the eventual build-up of condensed water on the thermoelectric cooler and the desiccant as the dehumidifier processed a humid gas stream. The dehumidifier would start to lose efficacy in matter of minutes, and water vapor would break through the dehumidifier. The gas sensing procedure in FIG. 5F was thus modified to address this issue. In that regard, instead of delivering acetone to the sensor in 5-minute pulses followed by 10-minute purges as done in the studies of FIG. 5A, acetone was delivered to the sensor in 3 minute back to back segments of increasing concentrations from 0.96 to 1,000 ppm. This change in procedure allowed direct comparison between detecting acetone in both dry and humid condition after both types of gas streams were processed through the dehumidifier (FIG. 5G).

Figure 6A:
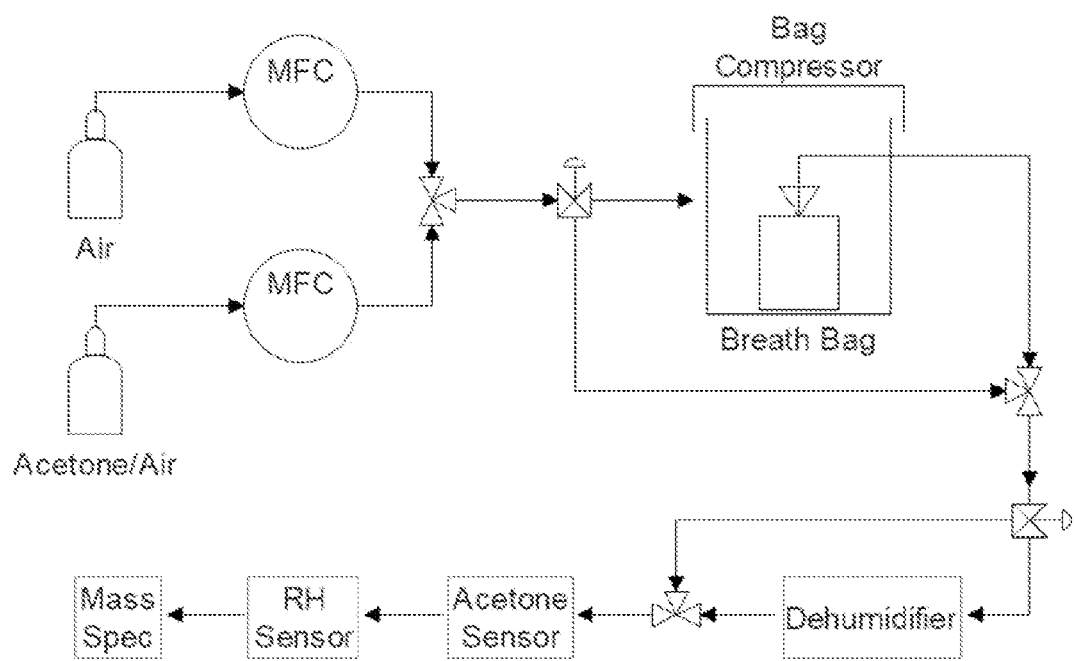
FIG. 6A illustrates schematically an embodiment of a gas delivery setup including a bag compressor used in connection with a breath bag in a number of studies of the devices, systems, and methods hereof wherein arrows indicate the direction of the gas flow.

To measure the contents of collected human breath samples, a gas delivery system was developed as illustrated in FIG. 6A. Calibration gases or breath samples were first collected in a 4-L TEDLAR gas (breath) bag. The breath bag was the placed inside a bag compressor, which was fabricated from a lever lock pail with an inlet port connected downstream of a mass flow controller or MFC and a tubing connector inside the pail that connected to the outlet port of the bag. When the pail was sealed and pressurized with air delivered from the MFC, the buildup of the pail's internal pressure caused the contents of the breath bag to empty through the outlet. The system of FIG. 6A allowed the contents of the breath bag to be delivered to the acetone sensor at a constant flow rate. A pair of three-way valves were installed to be able to by-pass the bag compressor and the dehumidifier. The acetone sensor hereof, a humidity sensor, and a mass spectrometer were placed downstream of the compressor to analyze the contents of the breath bag.

Figure 6B:
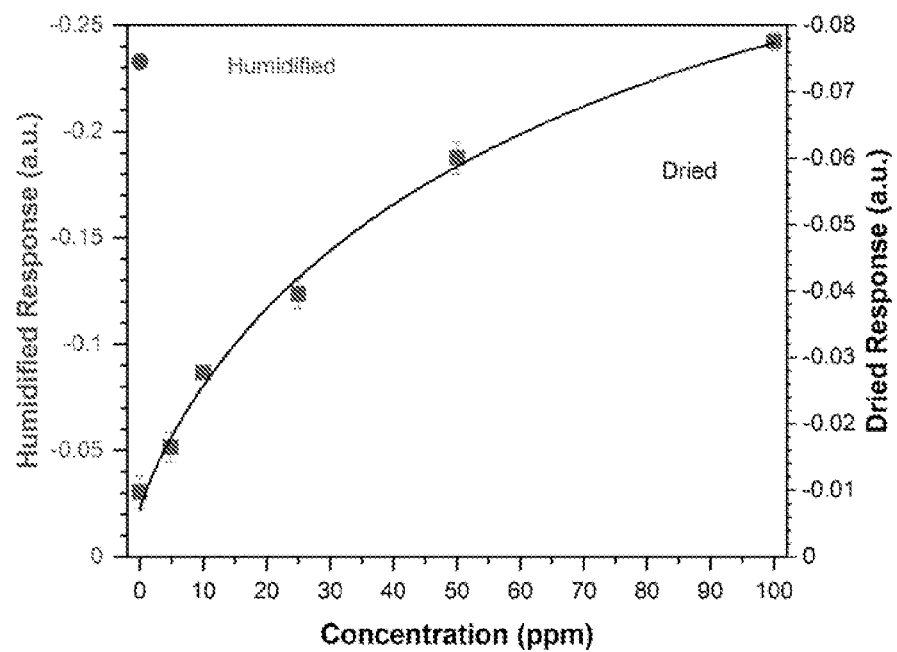
FIG. 6B illustrates calibration of chemiresistor devices hereof to a synthetic gas mixture composed of 100% RH, 5 vol % CO$_2$, and acetone delivered from the breath bag.

To calibrate the delivery system, a breath sampling bag was filled with known concentrations of acetone (0, 5, 10, 25, 50, 100 ppm) and 5 vol % $CO_2$ balanced in air saturated with water vapor. The synthetic air mixture represented the contents of an exhaled breath from a person in varying degree of ketosis. Approximately 30 seconds into exposure to the contents of the bag, the sensor unexpectedly started to increase in conductivity. About an additional 30 seconds later, the sensor started decreasing in conductivity as expected. The magnitude of the initial positive response was relatively constant, while the magnitude of later negative response correlated with the concentration of acetone. The mass spectrometer downstream of the sensor (see FIG. 6A) indicated that the initial positive response was due to carbon dioxide. The corresponding follow-on response was due to acetone breaking through the dehumidifier. The mass spectrum showed slow increase in the acetone trace (100 ppm) over time just above the noise level. The response to acetone was calculated by taking the difference between the peak current after the exposure to carbon dioxide and the current at the 3-minute mark. At this time point, the sensor had responded to the acetone and the water vapor started breaking through the dehumidifier. Three 0 ppm blank measurements were taken to calculate the detection limit for the breath sampling and delivery method. The interpolated detection limit from the calibration curve was 1.6 ppm (see FIG. 6B).

To demonstrate the feasibility of using the acetone sensor to detect acetone in human breath samples, breath samples were collected from three volunteers. Subjects 1 and 2 were on a self-directed low carbohydrate diet, while subject 3 did not restrict carbohydrates. Their breaths were sampled on multiple days and analyzed using the acetone sensor systems hereof. The breath samples were collected using the TEDLAR® gas sampling bag (available Sigma-Aldrich Corp of St. Louis, Missouri) from and delivered to the sensor using the bag compressor. The other two ketone bodies, BHB in the blood and AcAc in the urine, were also measured to compare the correlations between all three ketone bodies. BHB is the ketone found in the highest concentration in the blood. As the main indicator of ketosis, the other two measurement methods were compared to BHB.

Figure 7A:
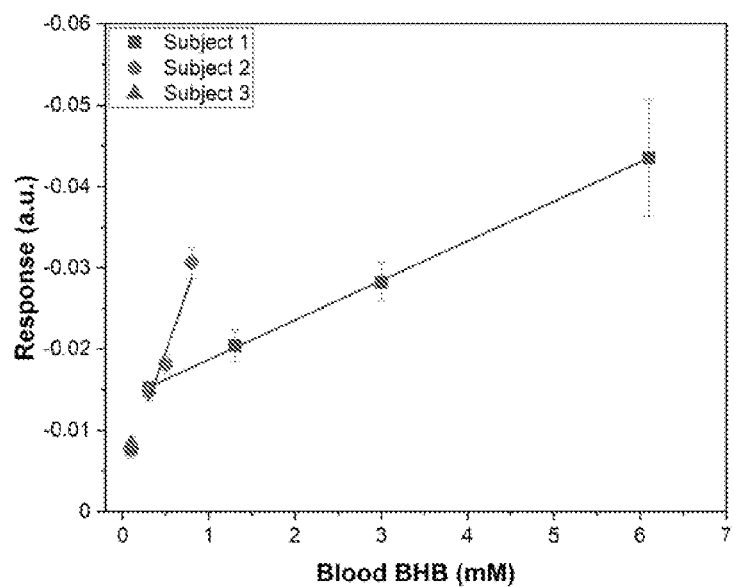
FIG. 7A illustrates correlation of blood BHB levels to sensor response after exposure to breath samples for three volunteer subjects.
Figure 7B:
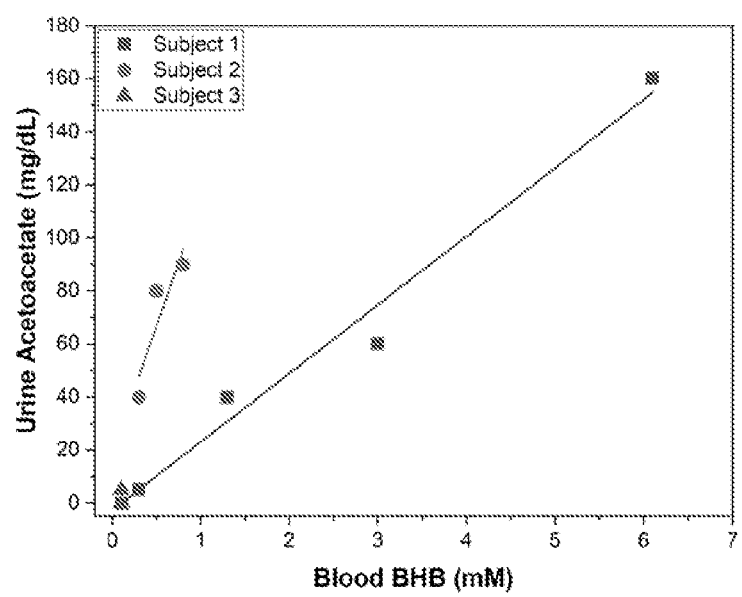
FIG. 7B illustrates AcAc measurements in the urine for three volunteer subjects.

The blood BHB concentration sampled from subject 1 had the widest concentration range between 0.1 mM and 6.1 mM. The measured blood BHB levels were linearly correlated to both breath ($r^2$=0.99) and urine ($r^2$=0.99) measurements (FIG. 7A). Subject 2 was in milder ketosis as measured in terms of BHB concentration. The correlation of BHB to the response of the acetone sensor ($r^2$=0.99) and AcAc ($r^2$=0.81) was also linear (FIG. 7B). Subject 3 produced only trace amounts of ketone bodies and the sensor trace was similar to the trace for 0 ppm reference. Compared to exposure to the reference standards, the devices hereof tended to continue to change in conductivity even after the 3 minutes of exposure to the breath samples. The continued response may, for example, be attributed to many of more than 3,400 known volatile organic compounds that are found in the human breath. However, the magnitude of the sensor response to breath samples increased proportionally to the concentration of BHB for all three volunteers indicating that the initial three minutes of the sensor response were due to acetone. Additional control experiments were performed to show that the sensor response was attributable to acetone by testing breath samples spiked with known volume of liquid acetone. Such ketone correlation studies demonstrated the feasibility of the acetone sensor devices, systems, and methods hereof to monitor nutritional ketosis.

To demonstrate that the acetone sensor may be incorporated as the sensing element of an acetone breathalyzer, a prototype was designed and fabricated. The prototype breathalyzer (as illustrated in FIGS. 8A through 8F) include a CC1110 (system-on-chip including a microcontroller unit or MCU available from Texas Instruments of Dallas, Texas) to function as the microcontroller, a 3D printed case or housing (FIGS. 8A through 8C) to house the electronics (FIGS. 8D through 8F), including, for example, a Wheatstone Bridge (FIGS. 8E and 8F) to measure the resistance of the sensor. A swappable and insertable sensor board (see, for example, FIGS. 8B and 8C) was designed to be plugged in and removed from the prototype similar to sensor board described in U.S. Patent Publication No. 2020/009342, the disclosure of which is incorporated herein by reference.

Figure 8A:
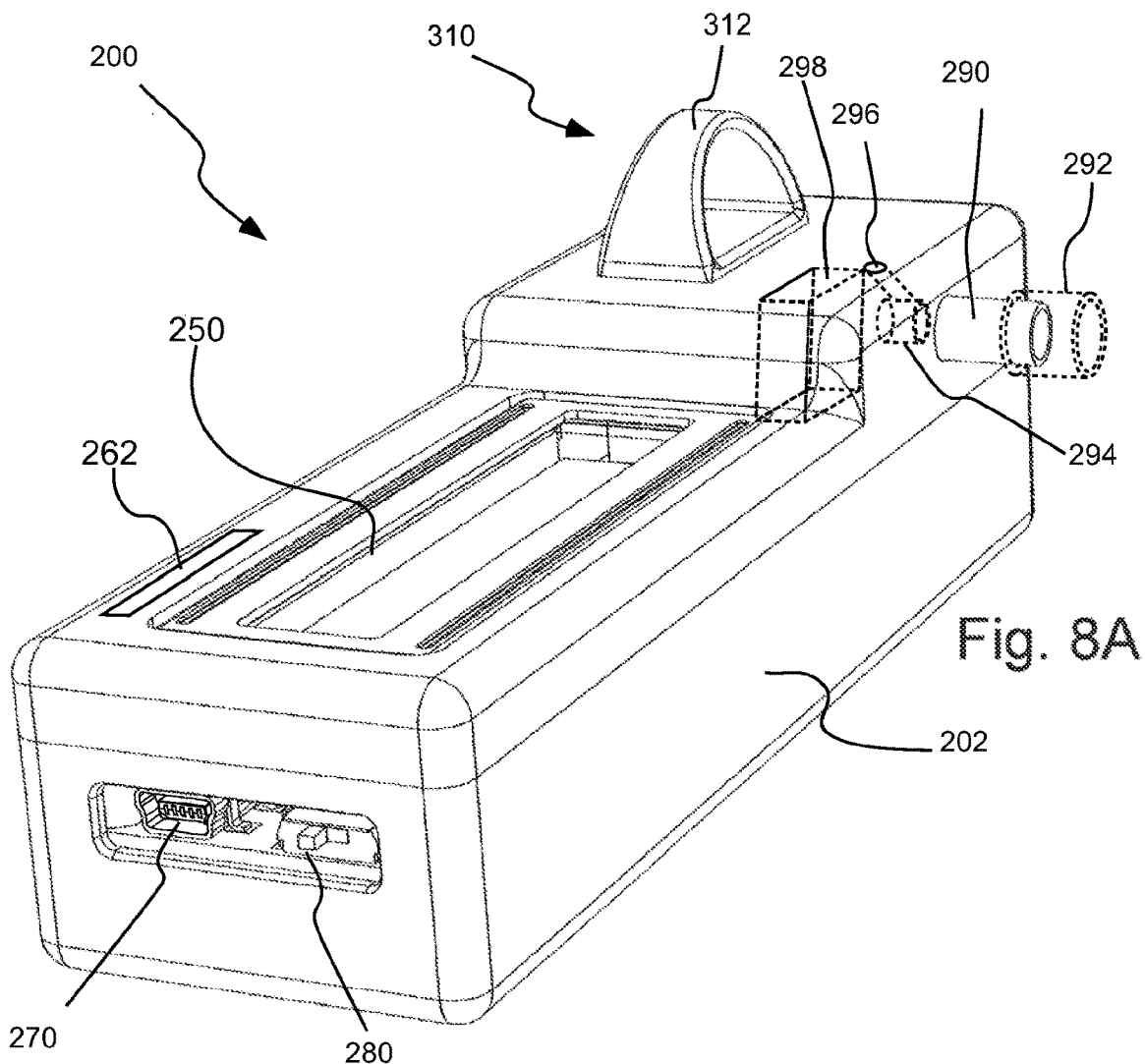
FIG. 8A illustrates a perspective view of an embodiment of a handheld breathalyzer system hereof.
Figure 8G:
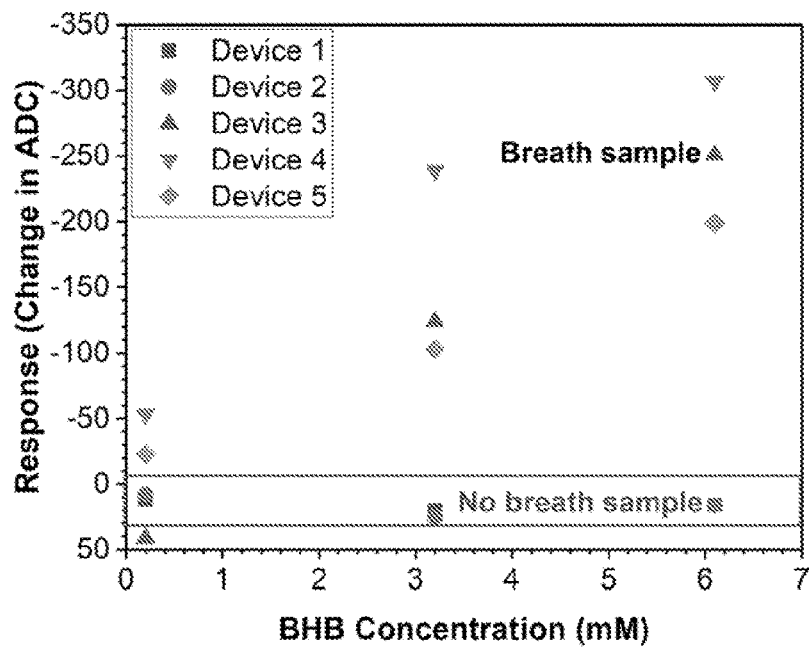
FIG. 8G illustrates measurement of breath samples using the system of FIG. 8A.
Figure 8B:
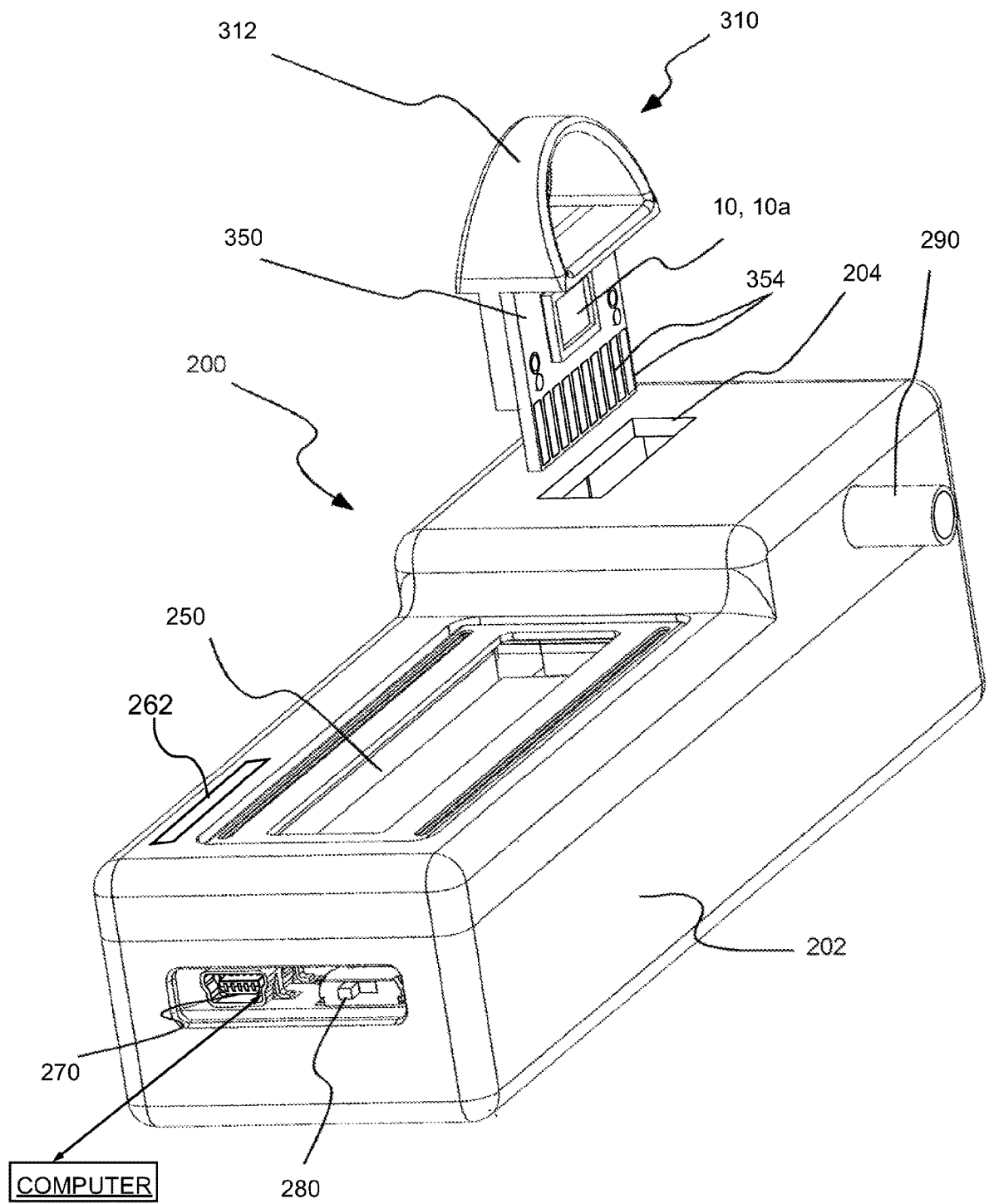
FIG. 8B illustrates a perspective view of an embodiment of the handheld breathalyzer system of FIG. 8A hereof wherein a sensor module is removed from the system.
Figure 8C:
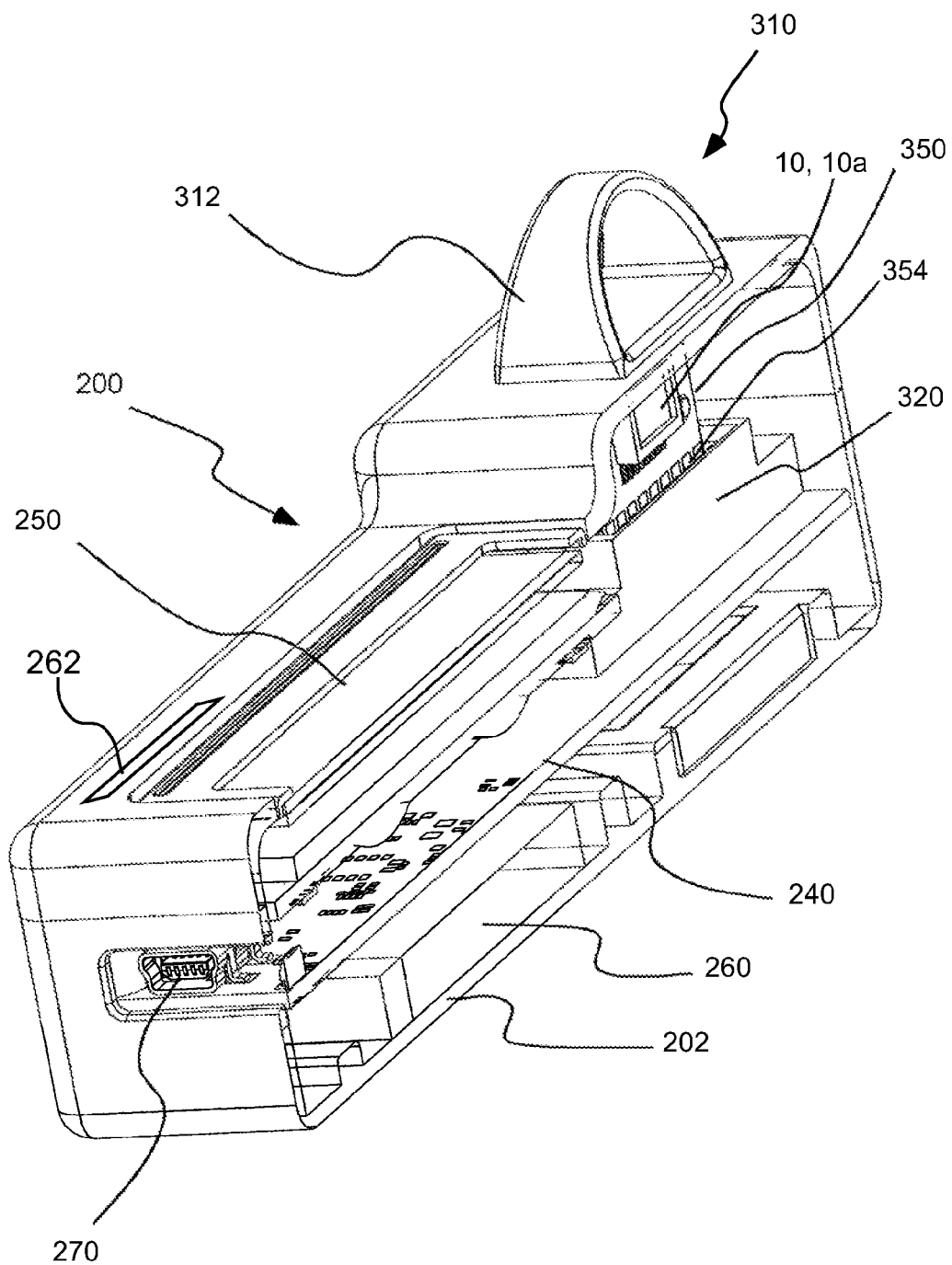
FIG. 8C illustrates a perspective, cutaway view of the handheld breathalyzer system of FIG. 8A.

In the embodiment illustrated in FIG. 8A through 8C, device or system 200 hereof for detection of acetone provides a relatively compact form. Device 200 includes a microchip-based sensor assembly 310 in which one or more chemiresistors 10 or field effect transistors (FETs) 10a is/are deposited on a silicon wafer 350 as illustrated in FIGS. 8B and 8C. Sensor assembly 310 is readily removably and operably attachable to a sensor assembly connector or receptacle 320 within breathalyzer housing 202 via a handle or gripping portion 312 on a first or outer end and conductive connectors 354 on a second or inner end. Sensor assembly 310 is placed in connection with a control board 240 (for example, a printed circuit board or PCB) via connector 220.

In the illustrated embodiment, sensor assembly 310 may be placed in and out of connection with connector or receptacle 320 via a slot or opening 204 formed in housing 202. The design of device 200 thereby facilitates removal of sensor assembly 310 for maintenance/replacement. A user may, for example, be provided with multiple sensor assemblies 310 in a system of kit for use in connection with device 200. Sensor assemblies 310, when removed from connection with device 200, may, for example, be serviced/refurbished or discarded.

Control board 240 includes or has attached thereto a controller system or processor system (not shown; including, for example, one or more microprocessors such as a CC1110 microprocessor) and a memory system (not shown) which is placed in operative or communication connection with the processor system via control board 240 or integrated with the processor system. Control board 240 is also in operative connection with a display 250 such as a liquid crystal display. A power supply/battery 260 (for example, a Lithium Polymer or LiPo battery) may be supplied to power one or more electronic circuitry components as described above. Such electric circuitry components are housed within a housing 202.

A mini USB or other communication port 270 in operative connection with control board 240 may extend through housing 202. Mini USB or other communication port 270 may, for example, be used to connect to a computer such as a general-purpose personal computer or PC (see, for example, FIG. 8B) to, for example, effect software revision and/or data transfer, to effect battery charging and/or to effect power the device (for example, even if battery 260 is absent or damaged) as known in the computer arts. An indicator 262 (for example, one or more LED lights) may be provided to set forth information such as battery status. Status indicator(s) 262 may, for example, indicate when battery 260 is low (RED), when the device is charging battery 260 (BLUE), and when charging of battery 260 is complete (GREEN). An on/off or power switch 280 may, for example, be provided on housing 202. A breath tube 290 passes through housing 202 and has an outlet in the vicinity of chemiresistor 10a or FET 10 of sensor assembly 210. A mouth piece 292 (shown in broken lines in FIG. 8A) may be provided at an inlet of breath tube 290.

As described above, it may be desirable to limit the flow of sample to the dehumidifier system and sensor(s) of systems hereof. This may be particularly important in the case of incorporation of a dehumidifier system into a housing of a device or system which may be handheld such as system 200. FIG. 8A illustrates schematically a system 294 to divert, reduce or limit flow in fluid connection with the assembly of inlet 290 and mouthpiece 292. System 294 may, for example, divert a portion of flow from the assembly of inlet 290 and mouthpiece 292 to a port 296 which is formed through housing 202. The remainder or non-diverted portion of the flow from the assembly of inlet 290 and mouthpiece 292 passes to a dehumidifier system 298 (which is in fluid connection with system 294) and then to sensor(s) 10, 10a as described above. The components of dehumidifier system 298 (that is, one or more condenser units and/or one or more desiccant units) are sufficiently reduced in volume or size to be encompassed within housing 202. Condenser units including a condensing chamber having microchannel-based heatsinks may, in certain embodiments, be used to assist in reducing size of the condenser unit while maintaining a relatively large surface area for heat exchange.

Methodologies/circuits for sensing changes in sensor resistance in device or system 200 are shown in FIGS. 8D through 8F. FIG. 8D illustrates a simple voltage divider configuration of resistors, where a change in resistance is converted to a change in voltage. In the voltage divider network, one resistor (R) is a fixed value, and the other resistance (RCNT) is variable, wherein RCNT represents the sensor resistance. In a number of embodiments, an analog-to-digital converter (ADC) is the input port of a digitizing device, such as a microcontroller/microprocessor. Sensing changes in RCNT is easier when the resistance change results in a larger voltage change. The point where the largest voltage change occurs will be when R equals the nominal sensor resistance before a measurement is taken (for example, R=RCNT).

In a number of embodiments, the resistor network in device 200 was a Wheatstone bridge as illustrated in FIG. 8E, which uses the same principle of voltage division described above but increases the resistance-sensing accuracy with a more complex resistor configuration as illustrated in FIG. 8D. Three of the resistor values are known. The fourth resistor value can be calculated from a measurement of the differential voltage between the centers of each "leg" of the bridge, labeled in FIG. 8E as Vwhtstn. Sensor 10, 10a forms the bottom half of one leg of the bridge. FIG.

8F illustrates an embodiment of electronic circuitry for system 200 as described further in the Experimental Examples section below.

Figure 8H:
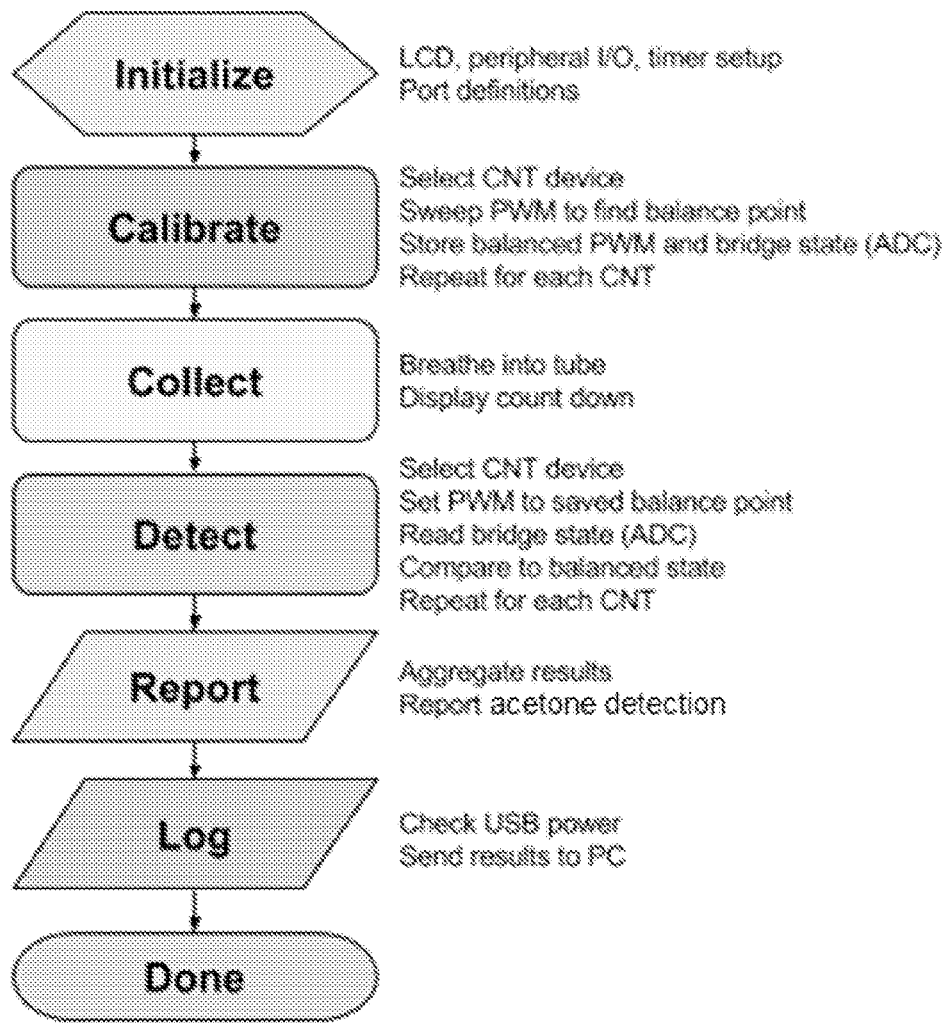
FIG. 8H illustrates an embodiment of a software algorithm for an operational or control protocol for the system of FIG. 8A.

To test device or system 200, sensor response to breath samples from subject 1 was measured and correlated to blood BHB concentration. Before delivering the breath sample to the sensor, system 200 was first powered on to find the voltage balance point for each sensor as a resistor in the Wheatstone bridge (FIGS. 8E and 8F). Once balanced, one of the two chips in the removable receptacle was directly exposed to the dried breath sample from a gas bag for 3 minutes. System 200 then displayed the voltage change from the initial balanced state of each sensor converted by the analog-to-digital convertor (ADC) as a hexadecimal number. Three of the devices that were exposed to breath samples showed linear correlation to the blood BHB levels, while the other two devices did not (see FIG. 8G). These results illustrate that acetone sensors hereof can be implemented into a handheld breathalyzer with circuitry that can measure changes in resistance. A representative protocol sequence (software algorithm) for system 200 in measuring breath acetone is illustrated in FIG. 8H.

A schematic illustration of another system hereof is illustrated in FIG. 1D. In the system of FIG. 1D, a drying system is provided to remove condensate water and/or desiccant-adsorbed water from the system. In the illustrated embodiment, the dehumidifier or dehumidifier system includes a condenser (as described above), a desiccant module (as described above), a valve and a fan. During operation, when a breath sample flows into the dehumidifier, the dehumidifying process has two stages, a condensation stage (stage 1 in the illustrated embodiment) and a drying stage (stage 2 in the illustrated embodiment). As the sample flows (for example, a breath sample) through the condenser, a portion of the water vapor will be condensed by removing the heat, Q, from the air sample using a thermoelectric cooler as described above. The remaining moisture (or at least a portion thereof) in the flow stream will then be absorbed by the desiccant module. Finally, the dehumidified/dried air stream will pass over the sensor (for example, an acetone sensor as describe above). The output from the sensor is measured to provide a concentration of the analyte (for example, acetone) in the sample. After the measurement of analyte is complete, the valve will be switched, and the fan (which may, in a number of embodiments, be used in connection with a heater to provide heated air flow) will be turned on to generate a dry air flow through the dehumidifier to dry the desiccant module and the condenser module. This system/methodology facilitates multiple uses of the dehumidifying system or module in, for example, a breathalyzer system. The design of the condenser and the desiccant module may, for example, be optimized to substantially or completely dry the air stream before it reaches the sensor.

Experimental Examples

Materials. Oxidized single-walled carbon nanotubes were obtained from Carbon Solutions Inc (P3-SWCNT) of Riverside, California USA. 200 proof ethanol was obtained from Decon Laboratories of King of Prussia, PA. Titanium isopropoxide (99.999% trace metals basis) and octadecane were obtained from Sigma Aldrich of St. Louis, Missouri USA. SYLGARD 184 polydimethylsiloxane (PDMS) was purchased from Fisher Scientific of Pittsburgh, Pennsylvania USA. All gas cylinders (9.6 ppm acetone balanced in air, 1,000 ppm acetone balanced in air, 10.5 vol % carbon dioxide balanced in nitrogen, ultra-zero grade air, argon grade 5.0) were sourced from Matheson Tri-Gas of Warren, New Jersey USA. The thermoelectric module, omnidirectional heat sink fins, and axial fans were purchased from Digi-Keys Electronics of Thief River Falls, Minnesota USA.

Silica gel, polypropylene film, and MYLAR film (polyethylene terephthalate) were purchased from Fisher Scientific. 3 Å molecular sieve, NAFION™ (a sulfonated tetrafluorethylene based fluoropolymer-copolymer), and calcium chloride were procured from Sigma Aldrich, and the SU-8 2075 solution and developer from Microchem Laboratory of Round Rock, Texas USA.

Sensor Material Synthesis and Device Fabrication. $TiO_2$ functionalized P3-SWCNT (SWCNT@$TiO_2$ core/shell nanohybrids) was synthesized based on a previously reported procedure. The as-synthesized material was composed of amorphous $TiO_2$ as expected. Silicon dies with 4 pairs of gold interdigitated electrodes were fabricated using standard photolithography procedures. Two silicon dies were wire bonded into a 40-pin dual inline pin (DIP) ceramic package (Kyocera) and potted using PDMS. The package was then heated to 120° C. on a hotplate. 5 µL of the SWCNT@$TiO_2$ solution was then drop-cast on to each of the chips and annealed for 30 minutes to evaporate off the water and set the nanotube network (FIG. 4, panels a-c).

Acetone Sensing Tests. The packaged chips were inserted into 40-pin zero insertion force (ZIF) connectors, pinhole mounted on a custom built-printed circuit board (PCB). The PCB was connected to a Keithley 2602B Source Meter Unit (SMU), which was used to measure the current of the chemiresistor at 50 mV every 0.5 second. A Keithley 3706A System Switch was used to multiplex current measurements among the 4 devices on each of the chips. Bronkhorst EL-FLOW Prestige mass flow controllers (MFC) connected to gas regulators on gas cylinders were used to deliver gases. A Bronkhorst Cori-Flow Coriolis MFC delivering deionized (DI) water to the Bronkhorst controlled evaporator mixer (CEM) was used to humidify the gas stream. Gases from the cylinders were either directly delivered to a machined TEFLON (a synthetic fluoropolymer of tetrafluoroethylene available from. The Chemours Company of Wilmington, Delaware USA) gas manifold sitting on top of the chemiresistor or used to pressurize the gas bag compressor and deliver its contents to the chemiresistor. The MFC, SMU, and System Switch were programmed and synchronized using LabView 2016. a system-design platform and development environment for a visual programming language available from National Instruments Corporation of Austin, Texas USA Response Calculation. Sensor response was calculated by taking the current at the start of the purge and subtracting it from the initial current before exposure to the analyte and dividing by the initial current.

$$\text{Response} = \frac{I_{initial} - I_{purge}}{I_{initial}}$$

Dehumidifier/Condenser. In a number of studies the dehumidifier included two stages of condensers and an inline desiccant. Each stage of the condenser was fabricated using a PDMS microchannel cooled by a thermoelectric module (40×40 mm CUI Devices CP85438). The hot side of the thermoelectric module was cooled by an aluminum container with octadecane as a phase change material (melting point 28-30° C.), omnidirectional heatsink fins, and an axial fan. The desiccant was packed into a 4 cm long 6.35 mm (inner diameter) TYGON 2375 tubing. During an experiment, the thermoelectric cooler was powered on for approximately two minutes to reach a steady state temperature. After each experiment, the thermoelectric cooler was purged with dry air for at least two hours to remove any condensed water. The desiccant plug was also replaced with fresh dry material.

Condenser Microchannel Fabrication. To make the silicon channel mold, a silicon wafer was cleaned with a wet etch (3 parts $H_2SO_4$:1 part 30% $H_2O_2$). On the cleaned wafer, approximately 200 μm thick SU-8 2075 film was casted by spin coating the SU-8 solution at 1250 rpm. The casted film was soft baked at 65° C. for 7 minutes followed by 95° C. for 30 minutes. A quartz emulsion mask with 500 μm wide and up to 36 mm long channels was used to cure the film with UV (350-400 nm) radiation for 60 seconds. The Post Exposure Bake (PEB) was done at 65° C. for 5 minutes followed by 95° C. for additional 15 minutes. The SU-8 developer (Microchem) was used to rinse and remove the uncured portions of the film. The developed film was then hard baked at 200° C. for 15 mins.

To fabricate the polydimethylsiloxane or PDMS microchannels, the silicon wafer mold was wrapped around with aluminum foil to make a temporary dish. Solution of SYLGARD 184 PDMS (10 elastomer:1 crosslinker) was poured into the mold and then placed in a vacuum desiccator to remove any air bubbles. The PDMS was cured at 150° C. for 15 minutes. The PDMS microchannel was cutout using a razor blade and peeled off from the mold. The holes for the inlet and outlet tubing were made using a PDMS puncher. The PDMS microchannel was treated with plasma and then bonded to a 40×40 mm sized silicon wafer.

Breath Bag Compressor. The breath bag compressor was fabricated using an 18.9 L steel round pail (Grainger) with a lever lock rid. A 6.35 mm barbed hose fitting was added to side of the pail as the inlet port and a 6.35 mm PTFE female connector was added to the opposite side of the inlet port as the outlet port.

Ketone Bodies Measurements. Blood BHB levels were measured using the Abbott Precision Xtra Blood Glucose and Ketone Monitoring System with Abbott Precision Xtra Ketone Test Strips. Urine AcAc concentrations were measured using KETOSTIX® test strips available from Bayer of Barmen, Germany. Breath samples were collected using 4 L TEDLAR® (a polyvinyl fluoride file available from DuPont de Nemours, Inc. of Wilmington, Delaware USA) gas sampling bags from Agilent Technologies of Santa Clara, California USA. The valve port of the sampling bag was connected to a 6.35 mm TEFLON tubing and a disposable plastic mouthpiece to sample the breath. The breaths were sampled at least 2 hours after any food or beverages were consumed to minimize the concentration of exogenous compounds in the samples.

Electron Microscopy. TEM images were taken using a FEI Morgagni microscope operating at an acceleration voltage of 80 keV. The SEM images were acquired using a SEM ZEISS Sigma500 VP microscope operating at an accelerating voltage of 3 kV.

Breathalyzer Prototype.

Electronics. The Power Management portion of the design converts either the +5V USB power (via the mini-USB port) or the 3.7V LiPo battery to a regulated 3.3V for the entire device's electronics. The battery charger/controller handles recharging the LiPo battery and simultaneously powering the system when the +5V USB connection is made.

The core of the System Control and Communication portion of the design is the CC1110 MCU. The MCU uses the I/O expander, via a 4-wire Serial Peripheral Interface (SPI) to enable each SWCNT@$TiO_2$ sensor individually. The MCU also writes messages to the LCD display. If the +5V USB connection is made, then the MCU can communicate with a computer host via USB through the USB-to-Serial Converter (FT232).

The PWM-to-DC Converter converts the Pulse-Width Modulation (PWM) signal output from the MCU to a direct current (DC) voltage. The conversion is accomplished through a filter network situated between two op-amp buffers.

The Wheatstone Bridge Instrumentation Amplifier, Wheatstone Bridge Balance Status, CNTx Load Switching, and Wheatstone Bridge are all tightly related and interconnected. The CNTx Load Switching portion is where a specific SWCNT@$TiO_2$ sensor load is switched into use via the MCU programming the I/O expander. Up to 7 sensors can be multiplexed. The Wheatstone Bridge uses four resistors, two sets of two resistors connected in series between the system supply voltage and ground. The voltage between the two series resistors in each of the two legs can be balanced by the PWM-to-DC Converter. The Wheatstone Bridge Balance Status activates when the Wheatstone Bridge has been balanced via the PWM-to-DC Converter. The Wheatstone Bridge Instrumentation Amplifier amplifies a difference between the two legs of the Wheatstone Bridge.

Device Enclosure and Assembly. The prototype device housing (case) was designed in SolidWorks (a solid modeling computer-aided design and computer-aided engineering computer program) available from Dassault Systemes of Vélizy-Villacoublay, France. The case was 3D printed in two pieces (top and bottom) using PLA filament. A separate piece was printed to hold the swappable sensor board, with a handle for insertion and removal.

After 3D printing the bottom of the case, heat-set threaded inserts (McMaster-Carr Part No. 93365A120) were inserted using a soldering iron. After soldering all components on the main PCB, the battery was connected by plugging the battery connector into the socket on the PCB. The battery was secured to the PCB with double-sided tape. Standoffs were positioned between the LCD and the circuit board for additional support. The board was then positioned in the bottom of the 3D-printed case. The top of the case was attached with #4-40 screws (the screws insert through the standoffs and the LCD board). A 16-pin SOIC package was soldered to the swappable sensor PCB. Silicon dies were then packaged into the SOIC package, and the assembled board was attached to the 3D-printed swappable insert with epoxy.

Software When the device is powered on, there is an initialization step in which the LCD and MCU functions and ports are set up. Following initialization, the device automatically calibrates by sweeping values of the PWM to find the balanced state of the Wheatstone bridge. The value of the Wheatstone bridge differential voltage is also stored for later comparisons, via the ADC. The calibration is performed for up to seven chemiresistors, with the calibration state stored for each sensor. The number displayed on the LCD screen while calibrating corresponds to each pad of the sensor insert. When the device is powered on, there is an initialization step in which the LCD and MCU functions and ports are set up. Following initialization, the device automatically calibrates by sweeping values of the PWM to find the balanced state of the Wheatstone bridge. The value of the Wheatstone bridge differential voltage is also stored for later comparisons, via the ADC. The calibration is performed for up to seven chemiresistors, with the calibration state stored for each sensor. The number displayed on the LCD screen while calibrating corresponds to each pad of the sensor insert.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A portable sensor system for detecting at least one analyte in an environment, comprising:
    a sensor which is responsive to the analyte; and
    a dehumidifier system in fluid connection with the sensor, the dehumidifier system comprising
        one or more condenser units, each of the one or more condenser units comprising a thermoelectric module comprising a cooling section and a heating section, the cooling section being positioned within a condensing chamber of the condenser unit, the condensing chamber being in fluid connection with the environment and with the sensor, the cooling section of the thermoelectric module comprising a first heatsink in operative connection with the cooling section, the first heatsink comprising a plurality of spaced plates or fins which define microchannels therebetween, the heating section of the thermoelectric module comprising a second heatsink in operative connection with the heating section; and
    electronic circuitry comprising at least one measurement system in operative connection with the sensor which is configured to measure a response of the sensor,
    wherein the condensing chamber further includes a desiccant material.

2. The portable sensor system of claim 1 wherein the portable sensor is configured to be handheld.

3. The portable sensor system of claim 1 wherein the dehumidifier system comprises a plurality of condenser units, wherein the plurality of condenser units are arranged in series or are arranged in parallel.

4. The portable sensor system of claim 3 wherein the plurality of condenser units are arranged in series.

5. The portable sensor system of claim 4 wherein the a hydrodynamic diameter of the microchannels of the plurality of spaced plates or fins is in the range of 1 µm to 1 mm.

6. The portable sensor system of claim 5 wherein the at least one analyte is acetone.

7. The portable sensor system of claim 5 wherein the sensor comprises a substrate and a sensor medium on the substrate, the sensor medium comprising at least one nanostructure, wherein at least one property of the sensor medium is dependent upon the presence of the at least one analyte, wherein the at least one measurement system is configured to measure a variable providing a measure of change in at least one property of the sensor medium which is dependent upon the presence of the at least one analyte.

8. The portable sensor system of claim 7 wherein the sensor medium comprises a plurality of nanostructures in contact with titanium dioxide, and the sensor system further comprises at least one energy source to apply electromagnetic radiation to the sensor medium for a period of time.

9. The portable sensor system of claim 8 wherein the plurality of nanostructures comprise carbon nanostructures.

10. The portable sensor system claim 9 wherein the titanium dioxide is mixed with the plurality of nanostructures, immobilized upon the plurality of nanostructures, or covalently attached to the plurality of nanostructures.

11. The portable sensor system of claim 10 wherein the portable sensor is configured to be handheld and the environment is human breath.

12. The portable sensor system of claim 8 wherein the plurality of nanostructures comprises a network of oxidized single-walled carbon nanotubes.

13. The portable sensor system of claim 8 wherein the energy source is a source of UV light.

14. The portable sensor system of claim 13 wherein the electronic circuitry is configured to establish a baseline for detection of the at least one analyte after application of the UV light for the period of time.

15. The portable sensor system of claim 1 wherein the heating section of the thermoelectric module of each of the one or more condenser units is positioned outside of the condensing chamber and the first heatsink comprises an extending member which extends into the condensing chamber.

16. The portable sensor system of claim 1 wherein a hydrodynamic diameter of the microchannels of the plurality of spaced plates or fins is in the range of 1 µm to 5 mm.

17. The portable sensor system of claim 16 wherein the system further comprises a fan in fluid connection with the second heatsink.

18. The portable sensor system of claim 16 wherein the dehumidifier system comprises a desiccant unit comprising a desiccant material and a quantity of the desiccant material of the desiccant unit is selected to limit removal of the at least one analyte for a given range of flow rate so that a sample reaching the sensor includes a concentration of analyte at or above a detection limit of the sensor.

19. The portable sensor system of claim 18 wherein the desiccant material of the desiccant unit comprises calcium chloride.

20. The portable sensor system of claim 19 further comprising a drying system to remove at least a portion of at least one of condensate water or water adsorbed on the desiccant material.

21. A method of detecting an analyte in an environment, comprising:
    passing a sample from the environment through a dehumidifier system of a portable sensor system, the dehumidifier system comprising one or more condenser units, each of the one or more condenser units comprising a thermoelectric module comprising a cooling section and a heating section, the cooling section being positioned within a condensing chamber of the condenser unit, the condensing chamber being in fluid connection with the environment and with the sensor, the cooling section of the thermoelectric module comprising a first heatsink in operative connection with the cooling section, the first heatsink comprising a plurality of spaced plates or fins which define microchannels therebetween, the heating section of the thermoelectric module comprising a second heatsink in operative connection with the heating section; and
    contacting the sample with a sensor of the portable sensor system in fluid connection with the dehumidifier system after the sample exits the dehumidifier system,
    wherein the condensing chamber further includes a desiccant material.

* * * * *